(12) United States Patent
Yamazaki et al.

(10) Patent No.: US 7,301,033 B2
(45) Date of Patent: Nov. 27, 2007

(54) PPAR-ACTIVATING COMPOUND

(75) Inventors: Yukiyoshi Yamazaki, Higashimurayama (JP); Tsutomu Toma, Kodaira (JP); Masahiro Nishikawa, Nagoya (JP); Hajime Yamada, Higashimurayama (JP); Hidefumi Ozawa, Hachiouji (JP); Ayumu Okuda, Higashimurayama (JP); Kazutoyo Abe, Mitaka (JP)

(73) Assignee: Kowa Co., Ltd., Nagoya-shi (JP)

( * ) Notice: Subject to any disclaimer, the term of this patent is extended or adjusted under 35 U.S.C. 154(b) by 0 days.

(21) Appl. No.: 11/335,669

(22) Filed: Jan. 20, 2006

(65) Prior Publication Data

US 2006/0167058 A1 Jul. 27, 2006

Related U.S. Application Data

(60) Provisional application No. 60/647,014, filed on Jan. 27, 2005.

(51) Int. Cl.
C07D 263/58 (2006.01)
A61K 31/423 (2006.01)

(52) U.S. Cl. ...................... 548/222; 514/375
(58) Field of Classification Search ................. 548/222
See application file for complete search history.

(56) References Cited

U.S. PATENT DOCUMENTS

| 5,741,796 A | 4/1998 | Hartman et al. |
| 6,653,334 B1 | 11/2003 | Yamazaki et al. |
| 2005/0070532 A1 | 3/2005 | Liu et al. |
| 2005/0101636 A1 | 5/2005 | Yamazaki et al. |

FOREIGN PATENT DOCUMENTS

| JP | 10-501222 | 2/1998 |
| WO | WO 02/46176 A1 | 6/2002 |
| WO | WO 2004/000762 A2 | 12/2003 |
| WO | WO 2004/092130 A2 | 10/2004 |
| WO | WO 2004/093879 A1 | 11/2004 |

OTHER PUBLICATIONS

Curtis et al., The Journal of the American Board of Family Practice, vol. 18, pp. 37-43, (2005).*
Isabelle Issemann, et al., "Activation of a member of the steroid hormone receptor superfamily by peroxisome proliferators", NATURE, vol. 347, Oct. 18, 1990, pp. 645-650.
Christine Dreyer, et al., "Control of the Peroxisomal β-Oxidation Pathway by a Novel Family of Nuclear Hormone Receptors", Cell, vol. 68, Mar. 6, 1992, pp. 879-887.
"A Unified Nomenclature System for the Nuclear Receptor Superfamily", Cell, vol. 97, Apr. 16, 1999, pp. 161-163.
Kristina Schoonjans, et al., "The peroxisome proliferator activated receptors (PPARs) and their effects on lipid metabolism and adipocyte differentiation", Biochimica et Biophysica Acta 1302, 1996, pp. 93-109.

Timothy M. Willson, et al., "The PPARs: From Orphan Receptors to Drug Discovery", Journal of Medicinal Chemistry, vol. 43, No. 4, Feb. 24, 2000, pp. 527-550.
Frank J. Gonzalez, et al., "Mechanism of Action of the Nongenotoxic Peroxisome Proliferators: Role of the Peroxisome Proliferator-Activated Receptor α", Journal of the National Center Institute, vol. 90, No. 22, Nov. 18, 1998, pp. 1702-1709.
Jean-Charles Fruchart, et al., "Peroxisome proliferator-activated receptor-alpha activators regulate genes governing lipoprotein metabolism, vascular inflammation and atherosclerosis", Current Opinion in Lipidology, 10, 1999, pp. 245-257.
Johan Auwerx, et al., "Regulation of Triglyceride Metabolism by PPARs: Fibrates and Thiazolidinediones have Distinct Effects", Journal of Atherosclerosis and Thrombosis, vol. 3, No. 2, 1996, pp. 81-89.
Bart Staels, et al., "Role of PPAR in the Pharmacological Regulation of Lipoprotein Metabolism by Fibrates and Thiazolidinediones", Current Pharmaceutical Design, vol. 3, No. 1, 1997, pp. 1-14.
Ines Pineda, et al., "Peroxisome proliferator-activated receptor alpha in metabolic disease, inflammation, atherosclerosis and aging", Current Opinion in Lipidology, 10, 1999, pp. 151-159.
Joseph Vamecq, et al., "Medical significance of peroxisome proliferator-activated receptors", The Lancet, vol. 354, Jul. 10, 1999, pp. 141-148.
Sander J. Robins, "PPARα ligands and clinical trials: cardiovascular risk reduction with fibrates", Journal of Cardiovascular Risk, vol. 8, No. 4, 2001, pp. 195-201.
Juergen M. Lehmann, et al., "An Antidiabetic Thiazolidinedione Is a High Affinity Ligand for Peroxisome Proliferator-activated Receptor γ (PPARγ)*", The Journal of Biological Chemistry, vol. 270, No. 22, 1995, pp. 12953-12956.

(Continued)

*Primary Examiner*—Laura L. Stockton
(74) *Attorney, Agent, or Firm*—Oblon, Spivak, McClelland, Maier & Neustadt, P.C.

(57) ABSTRACT

The present invention provides a compound selectively activating PPARα, which is useful as a medicament. The present invention is specifically directed to a benzoic acid derivative represented by the following general formula (1):

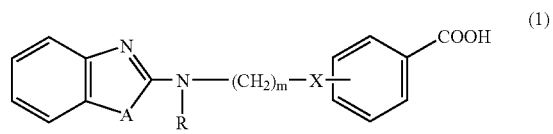

wherein A represents an oxygen atom, a nitrogen atom, or a sulfur atom; R represents a hydrogen atom, an alkyl group, an alkenyl group, an alkynyl group, a cycloalkyl group, a cycloalkyl-alkyl group, an aryl group, an aryl-alkyl group an aryl-oxy-alkyl group, a pyridyl-alkyl group, an alkoxycarbonyl-alkyl group, or a carboxy-alkyl group; X represents an oxygen atom, an NH group, or an $S(O)_n$ group (wherein n represents an integer of 0, 1, or 2); and m represents an integer from 2 to 8; or a salt thereof. The present invention also provides a medicament comprising the benzoic acid derivative or the salt thereof as an active ingredient.

11 Claims, No Drawings

OTHER PUBLICATIONS

Joel Berger, et al., "Thiazolidinediones Produce a Conformational Change in Peroxisomal Proliferator-Activated-γ: Binding and Activation Correlate with Antidiabetic Actions in db/db Mice", Endocrinology, vol. 137, No. 10, 1996, pp. 4189-4195.

Sander J. Robins, "PPARα ligands and clinical trials: cardiovascular risk reduction with fibrates", Journal of Cardiovascular Risk, vol. 8, No. 4, 2001, pp. 195-201.

Juergen M. Lehmann, et al., "An Antidiabetic Thiazolidinedione Is a High Affinity Ligand for Peroxisome Proliferator-activated Receptor γ (PPARγ)*", The Journal of Biological Chemistry, vol. 270, No. 22, 1995, pp. 12953-12956.

Joel Berger, et al., "Thiazolidinediones Produce a Conformational Change in Peroxisomal Proliferator-Activated-γ: Binding and Activation Correlate with Antidiabetic Actions in db/db Mice", Endocrinology, vol. 137, No. 10, 1996, pp. 4189-4195.

Mauricio J. Reginato, et al., "Mechanisms by which Thiazolidinediones Enhance Insulin Action", Trend Endocrinol. Metab., vol. 10, No. 1, 1999, pp. 9-13.

Akira Okuno, et al., "Troglitazone Increases the Number of Small Adipocytes without the Change of White Adipose Tissue Mass in Obese Zucker Rates", J. Clin. Invest., vol. 101, No. 6, Mar. 1998, pp. 1354-1361.

Sir-Pietrie, et al., "Glitazones and NIDDM", The Lancet, vol. 349, Mar. 29, 1997, p. 952.

Jennifer L. Oberfield, et al., "A peroxisome proliferator-activated receptor γ ligand inhibits adipocyte differentiation", Proc. Natl. Acad. Sci. vol. 96, May 1999, pp. 6102-6106.

Harold M. Wright, et al., "A Synthetic Antagonist for the Peroxisome Proliferator-activated Receptor γ Inhibits Adipocyte Differentiation", The Journal of Biological Chemistry, vol. 275, No. 3, Jan. 21, 2000, pp. 1873-1877.

Toshimasa Yamauchi, et al., "Inhibition of RXR and PPARγ ameliorates diet-induced obesity and type 2 diabetes", The Journal of Clinical Investigation, vol. 108, No. 7, Oct. 2001, pp. 1001-1013.

Didier Auboeuf, et al., "Tissue Distribution and Quantification of the Expression of mRNAs of Peroxisome Proliferator-Activated Receptors and Liver X Receptor-α in Humans", DIABETES, vol. 46, Aug. 1997, pp. 1319-1327.

William R. Oliver, Jr., et al., "A selective peroxisome proliferator-activated receptor σ agonist promotes reverse cholesterol transport", PNAS, vol. 98, No. 9, Apr. 24, 2001, pp. 5306-5311.

Yong-Xu Wang, et al., "Peroxisome-Proliferator-Activated Receptor σ Activates Fat Metabolism to Prevent Obesity", Cell, vol. 113, Apr. 18, 2003, pp. 159-170.

Helen Vosper, et al., "The Peroxisome Proliferator-activated Receptor σ Promotes Lipid Accumulation in Human Macrophages*", The Journal of Biological Chemistry, vol. 276, No. 47, Nov. 23, 2001, pp. 44258-44265.

Yaacov Barak, et al., "Effects of peroxisome proliferator-activated receptor σ on placentation, adiposity, and colorectal cancer", PNAS, vol. 99, No. 1, Jan. 8, 2002, pp. 303-308.

Barrie C. C. Cantello, et al., "[[ω-(Heterocyclylamino)alkoxy]benzyl]-2,4-thiazolidinediones as Potent Antihyperglycemic Agents", Journal of Medicinal Chemistry, vol. 37, No. 23, 1994, pp. 3977-3985.

* cited by examiner

PPAR-ACTIVATING COMPOUND

BACKGROUND OF THE INVENTION

1. Field of the Invention

The present invention relates to a PPAR-activating compound able to selectively activate a peroxisome proliferator-activated receptor α (PPARα) from among peroxisome proliferator-activated receptors (PPAR), which is useful as a medicament.

2. Description of the Related Art

PPAR is known as one of nuclear receptor families and is hitherto known to have three subtypes (α, γ, and δ) (Nature, 347, 645-650, 1990; Cell, 68, pp 879-887, 1992; Cell, 97, pp 161-163, 1999; Biochim. Biophys. Acta., 1302, pp 93-109, 1996; and Journal of Medicinal Chemistry, 43, pp 527-550, 2000).

Of these subtypes, PPARα is mainly expressed in the liver and is shown to be activated by plasticizers and fibrate drugs, for example, Wy14643 and commercially available medicaments such as clofibrate, fenofibrate, bezafibrate, and gemfibrozil (Journal of the National Cancer Institute, 90, 1702-1709, 1998; and Current Opinion in Lipidology, 10, pp 245-257, 1999).

PPARα activation is known to accelerate fatty acid β-oxidation in mammals, leading to decrease triglyceride in the blood. In humans, PPARα activation decreases lipids in the blood such as low density lipoprotein (LDL) cholesterol and very low density lipoprotein (VLDL) cholesterol, and PPARα-activating drugs are useful as preventive or therapeutic agents for hyperlipidemia and so on. Moreover, the PPARα-activating drugs increase in high density lipoprotein (HDL) cholesterol and suppress the expression of VCAM-1, a cell adhesion molecule, in blood vessels, and as such, are also considered to be useful as preventive or therapeutic agents for arteriosclerosis and so on. Additionally, the PPARα-activating drugs are also considered to be useful in the prevention or treatment of diabetes and inflammatory diseases, in addition to cardiac diseases (Journal of Atherosclerosis and Thrombosis, 3, pp 81-89, 1996; Current Pharmaceutical Design, 3, pp 1-14, 1997; Current Opinion in Lipidology, 10, pp 151-159, 1999; Current Opinion in Lipidology, 10, pp 245-257, 1999; The Lancet, 354, pp 141-148, 1999; Journal of Medicinal Chemistry, 43, pp 527-550, 2000; and Journal of Cardiovascular Risk, 8, pp 195-201, 2001).

On the other hand, PPARγ is mainly expressed in adipocytes and is known to play an important role in the differentiation and proliferation of in adipocytes. Thiazolidine derivatives, for example, drugs such as troglitazone, pioglitazone, and rosiglitazone, are known as PPARγ activators. These drugs have been reported to improve insulin resistance by inducing smaller, highly insulin-sensitive in adipocytes to replace fully-differentiated adipocytes with reduced insulin sensitivity (Journal of Biological Chemistry, 270, 12953-12956, 1995; Endocrinology, 137, pp 4189-4195, 1996; Trends Endocrinol. Metab., 10, pp 9-13, 1999; and J. Clin. Invest., 101, pp 1354-1361, 1998). However, these drugs have also been reported to have unfavorable effects of causing weight gains and obesity attributed to increased fats in humans (The Lancet, 349, pp 952, 1997). Recent reports indicate that PPARγ antagonists are also likely to improve insulin resistance (Proc. Natl. Acad. Sci., 96, pp 6102-6106, 1999; The Journal of Biological Chemistry, 275, pp 1873-1877, 2000; and J. Clin. Invest., 108, 1001-1013, 2001).

Alternatively, PPARδ is ubiquitously present in body and has been reported to participate in lipid metabolism. However, there have been only a few reports about highly selective PPARδ activators, and the biological significance of PPARδ has remained unclear. Currently, the structures of PPARδ activators have been reported in many bibliographies (Diabetes, 46, 1319-1327, 1997; and Journal of Medicinal Chemistry, 43, pp 527-550, 2000). According to a recent report, GW501516, a PPARδ activator, elevates HDL levels in monkeys (Proc. Natl. Acad. Sci., 98, pp 5306-5311, 2001). Moreover, it has also been reported that activated PPARδ expressed in adipocytes or skeletal muscle cells promotes fat burning (Cell, 113, pp 159-170, 2003). Meanwhile, compound F disclosed as a PPARδ activator in WO 97/28149 has been reported to have unfavorable effects of promoting lipid accumulation in human macrophages (Journal of Biological Chemistry, 276, pp 44258-44265, 2001). In addition, experiments using PPARδ-deficient mice suggest that PPARδ activation contributes to lipid-accumulating effects (Proc. Natl. Acad. Sci., 99, pp 303-308, 2002). These phenomena are seen as mutually contradictory effects in the progression and treatment of arteriosclerosis. Accordingly, the therapeutic significance of PPARδ can be said to remain unclear.

From the viewpoint of the above, PPARα-selective activators that minimally activate PPARγ and PPARδ are expected to be useful in the prevention and treatment of hyperlipidemia, arteriosclerosis, diabetes, diabetes complications, inflammation, cardiac diseases, and soon, without weight gains and obesity.

Although some compounds activating PPARα have recently been reported (e.g., WO 02/046176, WO 04/000762, and WO 04/092130), these compounds cannot be said to be PPARα-selective. Under the present circumstances, there remains unfound about highly PPARα-selective compounds useful in the prevention or treatment of the diseases described above.

SUMMARY OF THE INVENTION

An object of the present invention is to provide a compound selectively activating PPARα, which is useful as a medicament.

The present inventors have conducted various studies and have consequently completed the present invention by finding out that a benzoic acid derivative or a salt thereof represented by the formula (1) described below selectively activates PPARα and is useful as a preventive or therapeutic agent for hyperlipidemia, arteriosclerosis, diabetes, diabetes complications, inflammation, cardiac diseases, and so on, without weight gains and obesity.

That is, the present invention relates to a benzoic acid derivative represented by the following general formula (1):

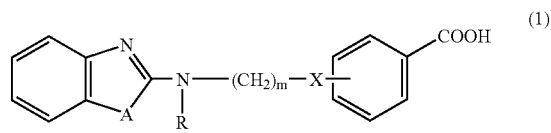

(1)

Wherein A represents an oxygen atom, a nitrogen atom, or a sulfur atom;

R represents a hydrogen atom, a $C_{1-8}$ alkyl group, a $C_{3-8}$ alkenyl group, a $C_{3-8}$ alkynyl group, a $C_{3-7}$ cycloalkyl group, a $C_{3-7}$ cycloalkyl-$C_{1-8}$ alkyl group, a $C_{6-10}$ aryl group, a $C_{6-10}$ aryl-$C_{1-8}$ alkyl group (wherein the $C_{6-10}$ aryl moiety may be substituted with one or two selected from a halogen atom, a hydroxy group, a nitro group, an amino group, a di-$C_{1-4}$ alkylamino group, a $C_{1-4}$ alkyl group, a $C_{1-4}$ alkoxy group, a benzyloxy group, a phenylsulfonylmethyl group, and a $C_{1-4}$ alkanesulfonyloxy group), a $C_{6-10}$ aryl-oxy-$C_{1-8}$ alkyl group (wherein the $C_{6-10}$ aryl moiety may be substituted with one or two selected from a halogen atom, a hydroxy group, a nitro group, an amino group, a di-$C_{1-4}$ alkylamino group, a $C_{1-4}$ alkyl group, a $C_{1-4}$ alkoxy group, a benzyloxy group, a phenylsulfonylmethyl group, and a $C_{1-4}$ alkanesulfonyloxy group), a pyridyl-$C_{1-8}$ alkyl group, a $C_{1-8}$ alkoxycarbonyl-$C_{1-8}$ alkyl group, or a carboxy-$C_{1-8}$ alkyl group;

X represents an oxygen atom, an NH group, or an $S(O)_n$ group (wherein n represents an integer of 0, 1, or 2); and m represents an integer from 2 to 8; or a salt thereof.

The present invention also relates to a compound selected from 3-[3-[N-(Benzoxazol-2-yl)-N-3-(4-chlorophenoxy) ethyl]aminopropoxy]benzoic acid, 2-[5-[N-(Benzoxazol-2-yl)-N-isopropyl]aminopentylthio]benzoic acid, 2-[5-[N-(Benzoxazol-2-yl)-N-n-butyl]aminopentylthio]benzoic acid, 2-[5-[N-(Benzoxazol-2-yl)-N-n-pentyl]aminopentylthio]benz oic acid, and salts thereof.

The present invention also relates to a medicament comprising the benzoic acid derivative or the salt thereof as an active ingredient.

The present invention also relates to a preventive or therapeutic agent for hyperlipidemia comprising the benzoic acid derivative or the salt thereof as an active ingredient.

The present invention further relates to a preventive or therapeutic agent for arteriosclerosis comprising the benzoic acid derivative or the salt thereof as an active ingredient.

The present invention still further relates to a preventive or therapeutic agent for diabetes comprising the benzoic acid derivative or the salt thereof as an active ingredient.

The present invention relates to a preventive or therapeutic agent for diabetes complications comprising the benzoic acid derivative or the salt thereof as an active ingredient.

The present invention also relates to a preventive or therapeutic agent for inflammation comprising the benzoic acid derivative or the salt thereof as an active ingredient.

The present invention further relates to a preventive or therapeutic agent for cardiac diseases comprising the benzoic acid derivative or the salt thereof as an active ingredient.

The present invention still further relates to a pharmaceutical composition comprising the benzoic acid derivative or the salt thereof and a pharmaceutically acceptable carrier.

The present invention yet further relates to a preventive or therapeutic method for hyperlipidemia comprising administering the benzoic acid derivative or the salt thereof.

The present invention also relates to a preventive or therapeutic method for arteriosclerosis comprising administering the benzoic acid derivative or the salt thereof.

The present invention further relates to a preventive or therapeutic method for diabetes comprising administering the benzoic acid derivative or the salt thereof.

The present invention still further relates to a preventive or therapeutic method for diabetes complications comprising administering the benzoic acid derivative or the salt thereof.

The present invention yet further relates to a preventive or therapeutic method for inflammation comprising administering the benzoic acid derivative or the salt thereof.

The present invention also relates to a preventive or therapeutic method for cardiac diseases comprising administering the benzoic acid derivative or the salt thereof.

The benzoic acid derivative or the salt thereof of the present invention represented by the formula (1) has the effect of selectively activating PPARα from among PPAR subtypes and is useful as a preventive or therapeutic agent for hyperlipidemia, arteriosclerosis, diabetes, diabetes complications, inflammation, cardiac diseases, and so on, without weight gains and obesity.

DETAILED DESCRIPTION OF THE PREFERRED EMBODIMENTS

In the general formula (1), a $C_{1-8}$ alkyl group represented by R includes linear and branched alkyl groups such as methyl, ethyl, n-propyl, isopropyl, n-butyl, isobutyl, sec-butyl, tert-butyl, n-pentyl, isopenty, n-hexyl, isohexyl, n-heptyl, and n-octyl groups. Of these groups, methyl, ethyl, n-propyl, isopropyl, n-butyl, n-pentyl, n-hexyl, n-heptyl, and n-octyl groups are particularly preferred.

A $C_{3-8}$ alkenyl group represented by R includes linear and branched alkenyl groups such as vinyl, allyl, butenyl, pentenyl, and hexenyl groups.

A $C_{3-8}$ alkynyl group represented by R includes linear and branched alkynyl groups such as propargyl and butynyl groups.

A $C_{3-7}$ cycloalkyl group represented by R includes cyclopropyl, cyclobutyl, cyclopentyl, cyclohexyl, and cycloheptyl groups.

More preferable examples of a $C_{3-7}$ cycloalkyl-$C_{1-8}$ alkyl group represented by R include $C_{3-7}$cycloalkyl-$C_{1-4}$alkyl groups, concretely including cyclopropylmethyl, cyclopropylethyl, cyclohexylmethyl, cyclohexylethyl, and cyclohexylpropyl groups. Of these groups, cyclohexylmethyl groups are particularly preferred.

A $C_{6-10}$ aryl group represented by R includes phenyl and naphthyl groups. Of these groups, naphthyl groups are particularly preferred.

Preferable examples of a $C_{6-10}$ aryl-$C_{1-8}$ alkyl group represented by R include $C_{6-10}$ aryl-$C_{1-4}$ alkyl groups. Phenyl-$C_{1-4}$ alkyl and naphthyl-$C_{1-4}$ alkyl groups are more preferred. Concrete examples thereof include benzyl, phenethyl, phenylpropyl, phenylbutyl, naphthylmethyl, naphthylethyl, and naphthyl propyl groups. Of these groups, phenyl-$C_{1-4}$ alkyl groups are more preferred, and benzyl groups are particularly preferred.

The $C_{6-10}$ aryl moiety in the $C_{6-10}$ aryl-$C_{1-8}$ alkyl group may be substituted with one or two selected from a halogen atom, a hydroxy group, a nitro group, an amino group, a di-$C_{1-4}$ alkylamino group, a $C_{1-4}$ alkyl group, a $C_{1-4}$ alkoxy group, a benzyloxy group, a phenylsulfonylmethyl group, and a $C_{1-4}$ alkanesulfonyloxy group. In this context, the halogen atom includes chlorine, bromine, and fluorine atoms. The di-$C_{1-4}$ alkylamino group includes dimethylamino, diethylamino, and diisopropyl amino groups. The $C_{1-4}$ alkyl group includes methyl, ethyl, and isopropyl groups. The $C_{1-4}$ alkoxy group includes methoxy, ethoxy, n-propoxy, isopropoxy, and butoxy groups. The $C_{1-4}$ alkanesulfonyloxy group includes methanesulfonyloxy, ethanesulfonyloxy, and propanesulfonyloxy groups. More preferably, these substituents on the aryl moiety are one or two selected from a halogen atom, a nitro group, and a $C_{1-4}$ alkyl group. The substituents are still more preferably a halogen atom, particularly preferably a chlorine atom.

Preferable examples of a $C_{6-10}$ aryl-oxy-$C_{1-8}$ alkyl group represented by R include $C_{6-10}$ aryl-oxy-$C_{1-4}$ alkyl groups. Phenyl-oxy-$C_{1-4}$ alkyl groups are more preferred. Concrete examples thereof include phenyloxymethyl, phenyloxyethyl, phenyloxypropyl, and phenyloxybutyl groups. Of these groups, phenyloxyethyl and phenyloxypropyl groups are particularly preferred.

The $C_{6-10}$ aryl moiety in the $C_{6-10}$ aryl-oxy-$C_{1-8}$ alkyl group may be substituted with one or two selected from a halogen atom, a hydroxy group, a nitro group, an amino group, a di-$C_{1-4}$ alkylamino group, a $C_{1-4}$ alkyl group, a $C_{1-4}$ alkoxy group, a benzyloxy group, a phenylsulfonylmethyl group, and a $C_{1-4}$ alkanesulfonyloxy group. In this context, the halogen atom includes chlorine, bromine, and fluorine atoms. The di-$C_{1-4}$ alkylamino group includes dimethylamino, diethylamino, and diisopropylamino groups. The $C_{1-4}$ alkyl group includes methyl, ethyl, and isopropyl groups. The $C_{1-4}$ alkoxy group includes methoxy, ethoxy, n-propoxy, isopropoxy, and butoxy groups. The $C_{1-4}$ alkanesulfonyloxy group includes methanesulfonyloxy, ethanesulfonyloxy, and propanesulfonyloxy groups. Preferably, these substituents on the aryl moiety are a halogen atom, particularly preferably a chlorine atom.

Preferable examples of a pyridyl-$C_{1-8}$ alkyl group represented by R include pyridyl-$C_{1-4}$ alkyl groups, concretely including pyridylmethyl, pyridylethyl, and pyridylpropyl groups. More preferable examples of a $C_{1-8}$ alkoxycarbonyl-$C_{1-8}$ alkyl group include $C_{1-4}$ alkoxycarbonyl-$C_{1-4}$ alkyl groups, concretely including methoxycarbonylmethyl, ethoxycarbonylmethyl, propoxycarbonylmethyl, methoxycarbonylethyl, and ethoxycarbonylethyl groups. Preferable examples of a carboxy-$C_{1-8}$ alkyl group include carboxy-$C_{1-4}$ alkyl groups, concretely including carboxymethyl and carboxyethyl groups.

A salt of the benzoic acid derivative includes: alkali metal salts such as sodium salts and potassium salts; alkaline-earth metal salts such as calcium salts and magnesium salts; organic basic salts such as ammonium salts and trialkylamine salts; salts of mineral acids such as hydrochloride and sulfate; and salts of organic acids such as acetate.

The benzoic acid derivative of the present invention may be a solvate typified by a hydrate.

It is preferred that the benzoic acid derivative or the salt thereof of the present invention should be represented by the general formula (1), wherein A represents an oxygen atom, more preferably wherein X represents an oxygen atom or a sulfur atom, still more preferably wherein R represents a $C_{1-8}$ alkyl group or a $C_{6-10}$ aryl-oxy-$C_{1-8}$ alkyl group. In light of PPARα selectivity, a compound selected from 3-[3-[N-(Benzoxazol-2-yl)-N-3-(4-chlorophenoxy) ethyl] aminopropoxy]benzoic acid, 2-[5-[N-(Benzoxazol-2-yl)-N-isopropyl]aminopentylthio] benzoic acid, 2-[5-[N-(Benzoxazol-2-yl)-N-n-butyl]aminopentylthio]benzoic acid, 2-[5-[N-(Benzoxazol-2-yl)-N-n-pentyl]aminopentylthio] benzoic acid, and salts thereof is particularly preferred.

The compound of the present invention can be obtained by, for example, manufacturing methods shown by reaction schemes A and B described below.

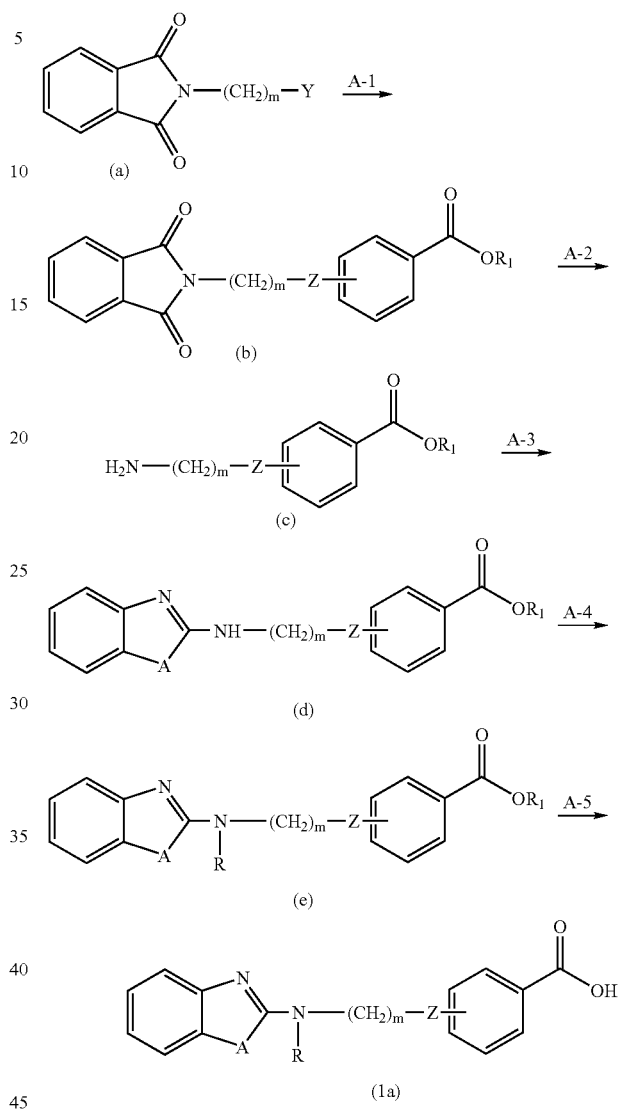

(in the formula, A, R, and m represent the same as above; $R_1$ represents a $C_{1-8}$ alkyl group; Y represents a halogen atom; and Z represents an oxygen atom, a sulfur atom, or an NH group.)

The manufacturing method shown by the reaction scheme A yields a compound (1a) of the present invention in the following steps: a monohalide (a) is obtained by the method described in Chemical and Pharmaceutical Bulletin (30 (5), pp 1579-1587, 1982) and then reacted with hydroxybenzoate or mercaptobenzoate; the resulting phthalimide (b) is treated with hydrazine to give an amine (c); this amine (c) is reacted with 2-halo-benzoazole to give a benzoazole (d); the benzoazole (d) is then reacted with any alkyl halide to give an ester (e); and the ester (e) is hydrolyzed to give the compound (1a)

The first step (A-1) is achieved by dissolving the monohalide (a) in a solvent such as DMF, THF, dioxane, or acetonitrile, which is then treated with required amounts of an inorganic base such as potassium carbonate ($K_2CO_3$), sodium carbonate ($Na_2CO_3$), or cesium carbonate ($Cs_2CO_3$)

and an organic base such as triethylamine or diisopropylethylamine and subsequently with a required amount of hydroxybenzoate or mercaptobenzoate, and then heated at room temperature to a temperature around the boiling point of the solvent with stirring for several hours to 24 hours. The ester is appropriately selected from tert-butyl ester, ethyl ester, methyl ester, and the like.

The second step (A-2) is achieved by dissolving the phthalimide (b) of the raw material in a solvent such as methanol, ethanol, or n-propanol, which is then reacted with a required amount of hydrazine and then heated at room temperature to a temperature around the boiling point of the solvent with stirring for several hours to 24 hours.

The third step (A-3) is achieved by dissolving the amine (c) of the raw material in a solvent such as DMF, THF, dioxane, or acetonitrile, which is then reacted with 2-halo-1,3-benzoazole such as 2-chlorobenzoxazole in the presence of required amounts of an inorganic base such as $K_2CO_3$, $Na_2CO_3$, or $Cs_2CO_3$ and an organic base such as triethylamine or diisopropylethylamine, and then stirred at room temperature to a temperature around the boiling point of the solvent for several hours to 24 hours, optionally under the atmosphere of inactive gas.

The fourth step (A-4) is achieved by dissolving the benzoazole (d) in a solvent such as DMF, THF, dioxane, or acetonitrile, which is then stirred together with any alkyl halide at room temperature to a temperature around the boiling point of the solvent in the presence of required amounts of an inorganic base such as $K_2CO_3$, $Na_2CO_3$, or $Cs_2CO_3$ and an organic base such as triethylamine or diisopropylethylamine for several hours to 24 hours.

When the resulting product is obtained in the form of ester such as methyl ester or ethyl ester, which is easily hydrolyzed by an alkali, the fifth step (A-5) is achieved by dissolving the ester (e) in a solvent such as methanol, ethanol, or THF, which is then treated with a base such as lithium hydroxide, sodium hydroxide, or potassium hydroxide, or an aqueous solution thereof, and reacted for several hours to 24 hours under cooling or at room temperature to a temperature around the boiling point of the solvent, followed by acidification with an acid such as hydrochloric acid. Alternatively, when the resulting product is obtained in the form of ester such as tert-butyl ester, which is easily decomposed by an acid, the fifth step (A-5) is achieved by dissolving the ester (e) in a solvent such as dichloromethane or chloroform, which is then treated with an acid such as trifluoroacetic acid and then stirred for several hours to 24 hours under cooling or at room temperature.

Reaction scheme B

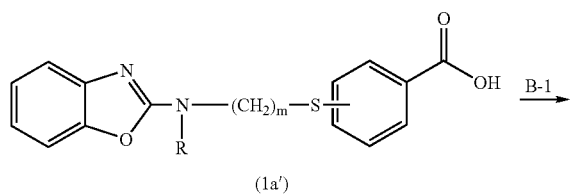

(1a')

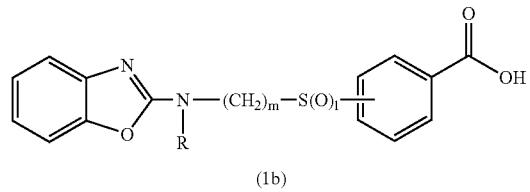

(1b)

[in the formula, R and m represent the same as above; and l represents an integer of 1 or 2.]

The manufacturing method shown by the reaction scheme B yields sulfoxy and sulfone forms (1b) from a compound (1a') of the present invention obtained in the reaction step A-5.

In the first step (B-1), the compound (1a') of the present invention is dissolved in a solvent such as chloroform or dichloromethane and then oxidized with a peroxide such as m-chloroperoxybenzoic acid or $H_2O_2$. The reaction is achieved by stirring for several hours to 24 hours under cooling or at room temperature.

The compound of the present invention is obtained by the methods described above and optionally, can be purified using usual purification means such as recrystallization or column chromatography. The compound can optionally be converted to a desired salt or solvate described above by a routine method.

The compound of the present invention thus obtained has the effect of selectively activating PPARα as shown in Test Example below and as such, is useful as a preventive or therapeutic agent for hyperlipidemia, arteriosclerosis, diabetes, diabetes complications (e.g., diabetic nephropathy), inflammation, cardiac diseases, and so on, in mammals including humans, without weight gains and obesity.

A medicament of the present invention comprises the compound (1) of the present invention or the salt thereof as an active ingredient and can be used in a dosage form appropriately selected without particular limitations according to therapeutic purposes, which may be any of oral solid preparations, oral liquid preparations, injections, suppositories, topical agents, eye drops, nasal drops, ear drops, and adhesive preparations. The medicament in any of these dosage forms can be manufactured by a common preparation method known by those skilled in the art by mixing the compound (1) of the present invention with a pharmaceutically acceptable carrier.

When the oral solid preparation is prepared, the compound (1) of the present invention can be supplemented with an excipient and optionally with a binder, a disintegrant, a lubricant, a coloring agent, a flavoring agent, an odor-improving agent, and so on, and then processed into a tablet, a granule, a powder, a capsule, or the like, by a routine method. Such additives may be those generally used in the art and can be exemplified by: milk sugar, sodium chloride, grape sugar, starch, microcrystalline cellulose, and silicic acid as the excipient; water, ethanol, propanol, simple syrup, gelatin solutions, hydroxypropylcellulose, methylcellulose, ethylcellulose, shellac, calcium phosphate, and polyvinylpyrrolidone as the binder; agar powder, sodium hydrogencarbonate, sodium lauryl sulfate, and stearic acid monoglyceride as the disintegrant; purified talc, stearate, borax, and polyethylene glycol as the lubricant; β-carotene, yellow iron sesquioxide, and caramel as the coloring agent; and white sugar and orange peels as the flavoring agent.

When the oral liquid preparation is prepared, the compound (1) of the present invention can be supplemented with a flavoring agent, a buffer, a stabilizer, a preservative, and so on, to manufacture an oral liquid medicine, a syrup, an elixir, or the like by a routine method. Such additives may be those generally used in the art and include white sugar as the flavoring agent, sodium citrate as the buffer, traganth as the stabilizer, and p-hydroxybenzoic acid ester as the preservative.

When the injection is prepared, the compound (1) of the present invention can be supplemented with a pH regulator, a stabilizer, a tonicity agent, and so on, to manufacture hypodermic, intramuscular, and intravenous injections by a routine method. Such additives may be those generally used in the art and can be exemplified by sodium phosphate as the pH regulator, sodium pyrosulfite as the stabilizer, and sodium chloride as the tonicity agent.

When the suppository is prepared, the compound (1) of the present invention can be supplemented with a carrier and a surfactant to manufacture the suppository by a routine method. Such additives may be those generally used in the art and can be exemplified by polyethylene glycol and hard fat as the carrier and polysorbate 80 as the surfactant.

When the topical agent is prepared, the compound (1) of the present invention can be supplemented with a base, a water-soluble polymer, a solvent, a surfactant, a preservative, and so on, to manufacture a liquid medicine, a cream medicine, a gel medicine, an ointment, or the like, by a routine method. Such additives include: liquid paraffin, white Vaseline, and purified lanolin as the base; carboxyvinyl polymer as the water-soluble polymer; glycerin and water as the solvent; polyoxyethylene fatty acid ester as the surfactant; and p-hydroxybenzoic acid ester as the preservative.

When the eye drop is prepared, the compound (1) of the present invention can be supplemented with a pH regulator, a stabilizer, a tonicity agent, a preservative, and so on, to manufacture the eye drop by a routine method. Such additives may be those generally used in the art and can be exemplified by sodium phosphate as the pH regulator, sodium pyrosulfite and EDTA as the stabilizer, sodium chloride as the tonicity agent, and chlorobutanol as the preservative.

When the nasal drop is prepared, the compound (1) of the present invention can be supplemented with a pH regulator, a stabilizer, a tonicity agent, a preservative, and so on, to manufacture the nasal drop by a routine method. Such additives may be those generally used in the art and can be exemplified by sodium phosphate as the pH regulator, sodium pyrosulfite and EDTA as the stabilizer, sodium chloride as the tonicity agent, and benzalkonium chloride, as the preservative.

When the ear drop is prepared, the compound (1) of the present invention can be supplemented with a pH regulator, a buffer, a stabilizer, a tonicity agent, a preservative, and so on, to manufacture the ear drop by a routine method. Such additives may be those generally used in the art and can be exemplified by sodium phosphate as the pH regulator and the buffer, sodium pyrosulfite and EDTA as the stabilizer, sodium chloride as the tonicity agent, and benzalkonium chloride as the preservative.

When the adhesive preparation is prepared, the compound (1) of the present invention can be supplemented with an adhesive, a solvent, a cross-linking agent, a surfactant, and so on, to manufacture a wet adhesive preparation, an adhesive plaster, or the like, by a routine method. Such additives may be those generally used in the art and can be exemplified by: partially neutralized polyacrylic acid, sodium polyacrylate, 2-ethylhexyl polyacrylate, and styrene-isoprene-styrene block copolymers as the adhesive; glycerin and water as the solvent; dihydroxy aluminum aminoacetate and dried aluminum hydroxide gel as the cross-linking agent; and polyoxyethylene fatty acid ester as the surfactant.

The dose of the medicament of the present invention varies depending on, for example, ages, body weights, dosage forms, and the number of doses. In general, it is preferred that the medicament should be administered orally or parenterally to an adult at one dose or in several separate doses, of 1 to 1000 mg per day in terms of the amount of the compound (1) of the present invention.

EXAMPLE

Hereinafter, the present invention will be described with reference to Examples. However, the present invention is not intended to be limited to these Examples.

Production Example 1

Synthesis of methyl 3-(4-phthalimidobutoxy)benzoate

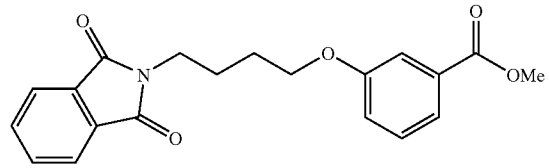

Methyl 3-hydroxybenzoate (3.0 g, 19.7 mmol) was dissolved in 50 mL of acetonitrile and $K_2CO_3$ (3.27 g, 23.7 mmol) was added. The resulting mixture was reacted with N-(4-bromobutyl)phthalimide (6.68 g, 23.7 mmol) and KI (3.93 g, 23.7 mmol) and stirred overnight at 70° C. Following the addition of water, the resulting mixture was extracted with chloroform. The organic layer was washed with brine. The organic layer was dried with sodium sulfate and then concentrated under reduced pressure, followed by recrystallization with n-hexane/ethyl acetate to give a white crystal (6.60 g, 94.8%).

$^1$H-NMR (400 MHz, $CDCl_3$) δ:

1.79-1.91 (m, 4H), 3.75 (t, J=7 Hz, 2H), 3.88 (s, 3H), 4.01 (t, J=6 Hz, 2H), 7.05 (ddd, J=8, 3, 1 Hz, 1H), 7.29 (t, J=8 Hz, 1H), 7.49 (dd, J=3, 2 Hz, 1H), 7.58 (dt, J=8, 1 Hz, 1H), 7.69 (d, J=3 Hz, 1H), 7.70 (d, J=3 Hz, 1H), 7.82 (d, J=3 Hz, 1H), 7.84 (d, J=3 Hz, 1H).

Production Example 2

Synthesis of methyl 3-(4-aminobutoxy)benzoate

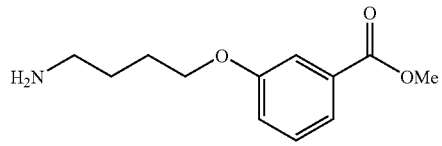

Methyl 3-(4-phthalimidobutoxy)benzoate (6.60 g, 18.68 mmol) was dissolved in 50 mL of ethanol and reacted with hydrazine monohydrate (1.87 g, 37.36 mmol). Following stirring at 80° C. for 1 hour, the resulting mixture was diluted with chloroform, then washed with a saturated sodium bicarbonate solution, water, and brine, and dried with sodium sulfate. The resulting reaction solution was concentrated under reduced pressure to give a white crystal (4.81 g). The white crystal was directly used in subsequent reaction.

Production Example 3

Synthesis of methyl 3-[4-(N-Benzoxazol-2-yl)aminobutoxy]benzoate

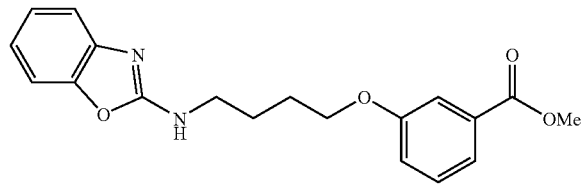

Methyl 3-(4-aminobutoxy)benzoate (4.81 g) was dissolved in 50.0 mL of tetrahydrofuran and N,N-diisopropylethylamine (2.90 g, 22.4 mmol) was added. Under cooling, 2-chlorobenzoxazole (3.44 g, 22.4 mmol) was added dropwise thereto and stirred overnight at room temperature. Following the addition of water, the resulting mixture was extracted with ethyl acetate. The organic layer was washed with brine. The organic layer was dried with sodium sulfate and then concentrated under reduced pressure, followed by purification by silica gel column chromatography (hexane:ethyl acetate=4:1) to give a compound of interest (3.22 g, 50.7%).

$^1$H-NMR (400 MHz, CDCl$_3$) δ:
1.66-1.75 (m, 2H), 1.85-1.95 (m, 2H), 3.54-3.61 (br, 2H), 3.91 (s, 3H), 4.06 (t, J=6 Hz, 2H), 5.23 (bs, 1H), 7.03 (t, J=8 Hz, 1H), 7.07-7.10 (m, 1H), 7.16 (t, J=8 Hz, 1H), 7.23 (d, J=8 Hz, 1H), 7.31-7.37 (m, 2H), 7.55 (s, 1H), 7.63 (d, J=8 Hz, 1H)

Production Example 4

Synthesis of methyl 3-[4-(N-Benzoxazol-2-yl)-N-n-propyl]aminobutoxy]benzoate

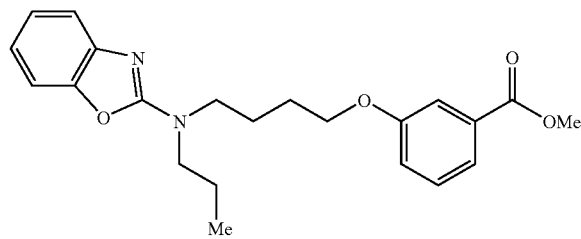

Methyl 3-[4-(N-Benzoxazol-2-yl)aminobutoxy]benzoate (4.0 g, 11.8 mmol) was dissolved in 5.0 mL of acetonitrile and cesium carbonate (4.97 g, 13.3 mmol) was added. Propyl iodide (2.59 g, 15.3 mmol) was then added dropwise to the reaction mixture. Following stirring overnight at 80° C., the resulting mixture was diluted with water and then extracted with ethyl acetate. The organic layer was washed with brine. The organic layer was dried with sodium sulfate and then concentrated under reduced pressure, followed by purification by silica gel column chromatography (hexane:ethyl acetate=7:1) to give a titled compound (3.3 g, 73%).

$^1$H-NMR (400 MHz, CDCl$_3$) δ:
0.97 (t, J=7 Hz, 3H), 1.68-1.77 (m, 2H), 1.84-1.95 (m, 4H), 3.50 (t, J=8 Hz, 2H), 3.58-3.67 (br, 2H), 3.91 (s, 3H), 4.02-4.12 (br, 2H), 6.98 (t, J=7 Hz, 1H), 7.07-7.16 (m, 2H), 7.22 (d, J=8 Hz, 1H), 7.31-7.37 (m, 2H), 7.55 (s, 1H), 7.62 (d, J=8 Hz, 1H)

Example 1

Synthesis of 3-[4-(N-(Benzoxazol-2-yl)-N-n-propyl)aminobutoxy]benzoic acid

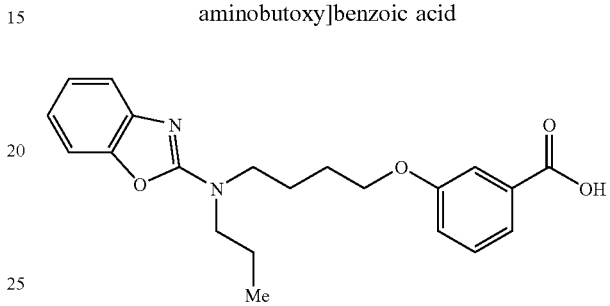

Methyl 3-[4-(N-Benzoxazol-2-yl)-N-n-propyl]aminobutoxy]benzoate (3.3 g, 8.57 mmol) was dissolved in 5.0 mL of methanol and 4.2 mL of 4.0 mol/L sodium hydroxide solution was added. After stirring at 80° C. for 3 hours, the resulting mixture was concentrated under reduced pressure. After addition of diluted hydrochloric acid, the reaction mixture was extracted with chloroform. The organic layer was washed with brine. The organic layer was dried with sodium sulfate and then concentrated under reduced pressure, followed by purification by silica gel column chromatography (chloroform:methanol=50:1) to give a titled compound (2.6 g, 82%).

$^1$H-NMR (400 MHz, CDCl$_3$) δ:
0.98 (t, J=7 Hz, 3H), 1.68-1.80 (m, 2H), 1.84-2.00 (br, 4H), 3.51 (t, J=8 Hz, 2H), 3.63 (t, 7 Hz, 2H), 4.05 (t, J=6 Hz, 2H), 6.99 (t, J=8 Hz, 1H), 7.09-7.17 (m, 2H), 7.23 (d, J=8 Hz, 1H), 7.34 (t, J=8 Hz, 1H), 7.40 (d, J=8 Hz, 1H), 7.60 (s, 1H), 7.70 (d, J=8 Hz, 1H)

Hereinafter, compounds of Examples 2 to 111 were synthesized in the same way as in Example 1.

Example 2

3-[4-(N-(Benzoxazol-2-yl)-N-methyl)aminobutoxy]benzoic acid

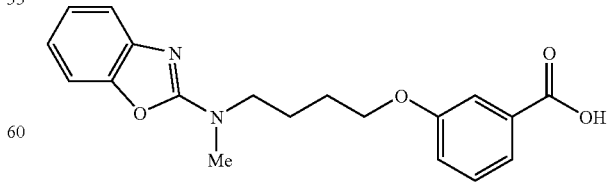

$^1$H-NMR (270 MHz, CDCl$_3$) δ: 1.79-1.99 (m, 4H), 3.23 (s, 3H), 3.56-3.73 (m, 2H), 3.98-4.14 (m, 2H), 7.00 (t, 1H, J=8H), 7.06-7.29 (m, 3H), 7.33 (d, J=9 Hz, 1H), 7.38 (t, J=9 Hz, 1H), 7.59 (s, 1H), 7.69 (d, J=8 Hz, 1H).

Example 3

3-[4-(N-(Benzoxazol-2-yl)-N-ethyl)aminobutoxy]benzoic acid

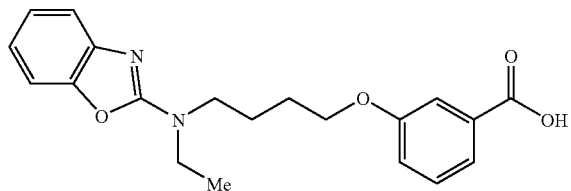

$^1$H-NMR (400 MHz, CDCl$_3$) δ:
1.30 (t, J=7 Hz, 3H), 1.81-1.98 (m, 4H), 3.56-3.68 (m, 4H), 4.05 (t, J=6 Hz, 2H), 6.99 (dt, J=8, 1 Hz, 1H), 7.10 (dd, J=8, 2 Hz, 1H), 7.15 (t, J=8 Hz, 1H), 7.24 (d, J=8 Hz, 1H), 7.34 (t, J=8 Hz, 1H), 7.41 (dd, J=8, 1 Hz, 1H), 7.61 (s, 1H), 7.70 (d, J=8 Hz, 1H)

Example 4

3-[4-(N-(Benzoxazol-2-yl)-N-n-butyl)aminobutoxy]benzoic acid

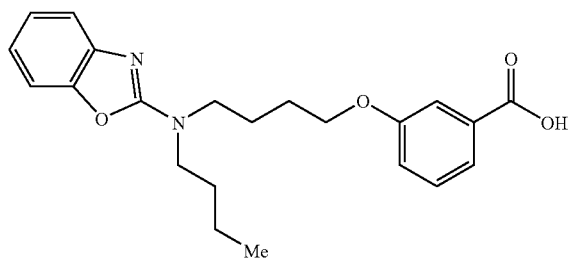

$^1$H-NMR (270 MHz, CDCl$_3$) δ: 0.97 (t, J=7 Hz, 3H), 1.40 (sextet, J=7 Hz, 2H), 1.69 (quintet, J=7 Hz, 2H), 1.78-1.97 (m, 4H), 3.54 (t, J=7 Hz, 2H), 3.60-3.62 (m, 2H), 3.97-4.09 (m, 2H), 6.99 (t, J=8 Hz, 1H), 7.08 (dd, J=8, 2 Hz, 1H), 7.15 (t, J=8 Hz, 1H), 7.24 (d, J=9 Hz, 1H), 7.32 (t, J=8 Hz, 1H), 7.42 (d, J=7 Hz, 1H), 7.56 (s, 1H), 7.70 (d, J=8 Hz, 1H)

Example 5

3-[3-[N-(Benzoxazol-2-yl)-N-3-phenoxypropyl]aminopropoxy]benzoic acid

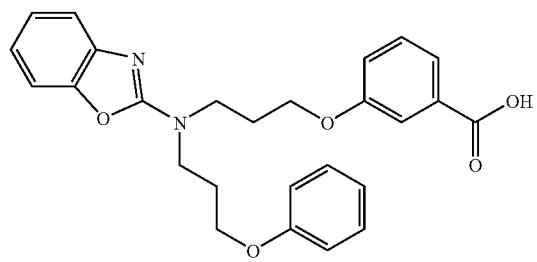

$^1$H-NMR (400 MHz, CD$_3$OD) δ: 2.20 (m, 4H), 3.78 (m, 4H), 4.05 (t, J=6 Hz, 2H), 4.10 (t, J=6 Hz, 2H), 6.85-6.87 (m, 3H), 6.95 (td, J=8, 1 Hz, 1H), 7.01 (dd, J=7, 2 Hz, 1H), 7.09-7.19 (m, 2H), 7.19-7.26 (m, 4H), 7.52-7.53 (m, 2H).

Example 6

3-[3-[N-(Benzoxazol-2-yl)-N-2-(4-chlorophenoxy)ethyl]aminopropoxy]benzoic acid

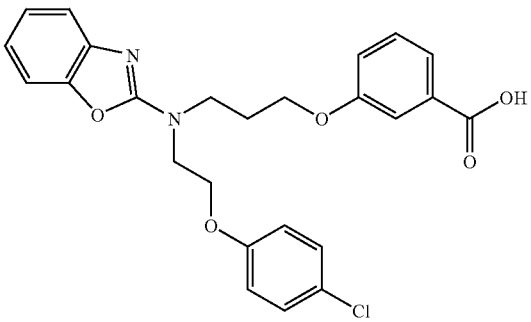

$^1$H-NMR (DMSO-d$_6$) δ:
2.16 (t, J=7 Hz, 2H), 3.79 (t, J=7 Hz, 2H), 3.91 (t, J=6 Hz, 2H), 4.08 (t, J=6 Hz, 2H), 4.26 (t, J=6 Hz, 2H), 6.95-7.00 (m, 4H), 7.19 (td, J=8, 1 Hz, 1H), 7.24 (t, J=8 Hz, 1H), 7.29-7.34 (m, 4H), 7.59 (dd, J=8, 2 Hz, 2H)

Example 7

2-[2-[N-(Benzoxazol-2-yl)-N-1-naphthylmethyl]aminoethoxy]benzoic acid

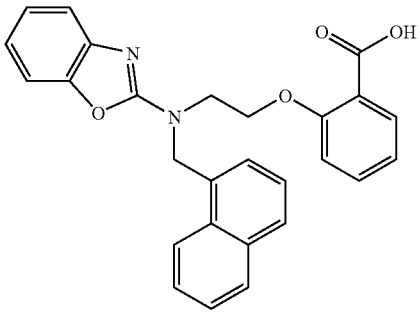

MS (m/z) 438 (M$^+$)

Example 8

2-[2-[N-(Benzoxazol-2-yl)-N-2-nitrobenzyl]aminoethoxy]benzoic acid

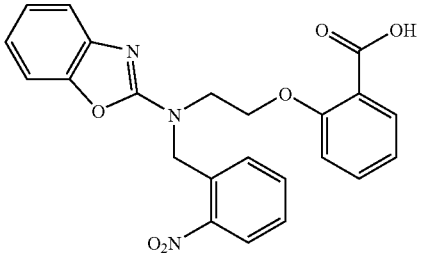

MS (m/z) 433 (M$^+$)

Example 9

2-[2-[N-(Benzoxazol-2-yl)-N-4-chlorobenzyl]amino-ethoxy]benzoic acid

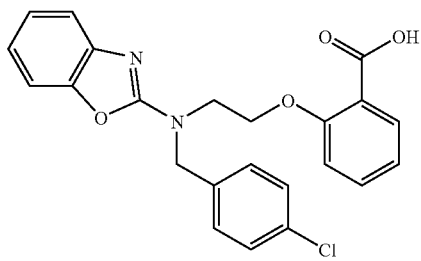

MS (m/z) 422 (M⁺), 424 (M⁺+2)

Example 10

2-[2-[N-(Benzoxazol-2-yl)-N-4-fluorobenzyl]amino-ethoxy]benzoic acid

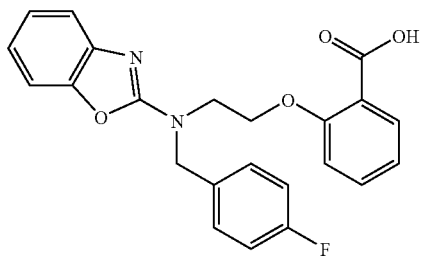

MS (m/z) 406 (M⁺)

Example 11

2-[2-[N-(Benzoxazol-2-yl)-N-n-butyl]aminoethoxy]benzoic acid

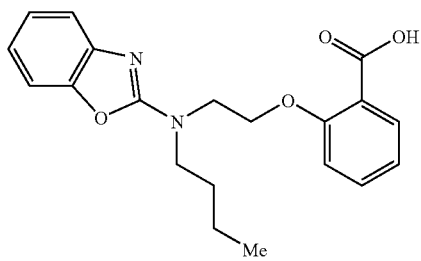

MS (m/z) 354 (M⁺)

Example 12

2-[2-[N-(Benzoxazol-2-yl)-N-n-heptyl]aminoethoxy]benzoic acid

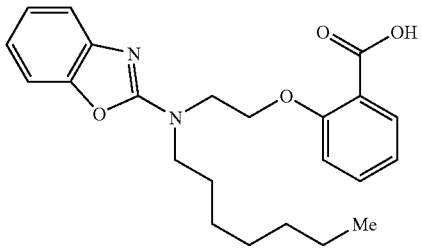

$^1$H-NMR (270 MHz, CDCl$_3$) δ:
0.85 (t, J=7 Hz, 3H), 1.21-1.33 (m, 8H), 1.70 (t, J=7 Hz, 2H), 3.64 (t, J=8 Hz, 2H), 4.04 (t, J=5 Hz, 2H), 4.48 (t, J=5 Hz, 2H), 6.94-7.13 (m, 3H), 7.16 (t, J=8 Hz, 1H), 7.27 (d, J=7 Hz, 1H), 7.40 (d, J=7 Hz, 1H), 7.50 (t, J=7 Hz, 1H), 8.09 (dd, J=8, 2 Hz, 1H).

Example 13

2-[2-[N-(Benzoxazol-2-yl)-N-n-octyl]aminoethoxy]benzoic acid

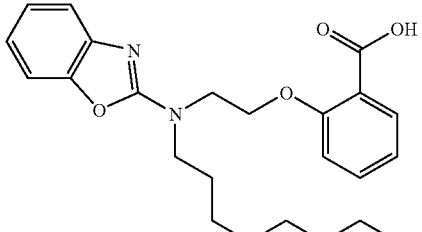

MS (m/z) 410 (M⁺)

Example 14

2-[2-[N-(Benzoxazol-2-yl)-N-n-propyl]aminoethoxy]benzoic acid

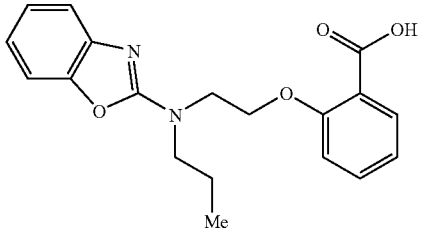

$^1$H-NMR (270 MHz, CDCl$_3$) δ: 0.97 (t, J=8 Hz, 3H), 1.67-1.81 (m, 2H), 3.62 (t, J=8 Hz, 2H), 4.04 (t, J=5 Hz, 2H), 4.47 (t, J=5 Hz, 2H), 6.91-7.10 (m, 3H), 7.16 (t, J=7 Hz, 1H), 7.27 (d, J=8 Hz, 1H), 7.40 (d, J=8 Hz, 1H), 7.47 (t, J=7 Hz, 1H), 8.08 (dd, J=8, 2 Hz, 1H)

Example 15

3-[3-[N-(Benzoxazol-2-yl)-N-4-chlorobenzyl]amino-propoxy]benzoic acid

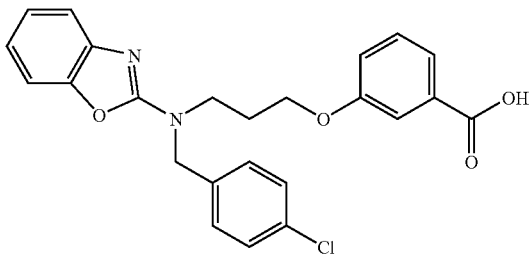

MS (m/z) 436 (M⁺), 438 (M⁺+2)

Example 16

3-[3-[N-(Benzoxazol-2-yl)-N-ethyl]aminopropoxy]benzoic acid

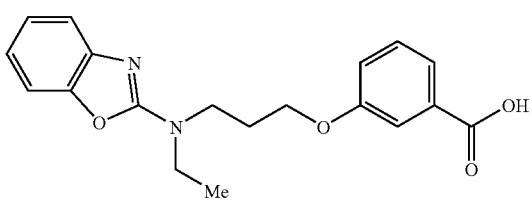

MS (m/z) 340 (M⁺)

Example 17

3-[3-[N-(Benzoxazol-2-yl)-N-methyl]aminopropoxy]benzoic acid

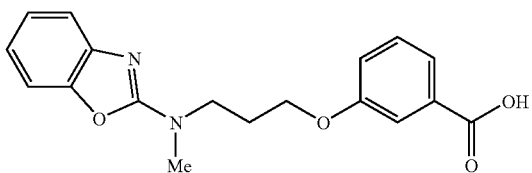

MS (m/z) 326 (M⁺)

Example 18

3-[3-[N-(Benzoxazol-2-yl)-N-n-butyl]aminopropoxy]benzoic acid

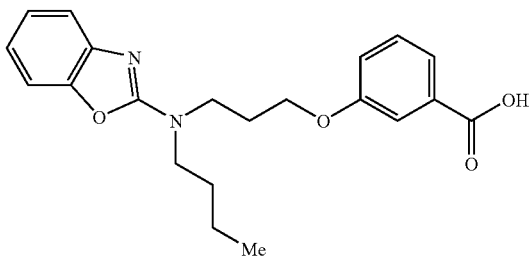

MS (m/z) 368 (M⁺)

Example 19

3-[3-[N-(Benzoxazol-2-yl)-N-n-heptyl]aminopropoxy]benzoic acid

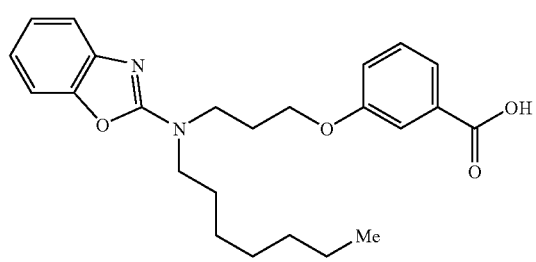

MS (m/z) 410 (M⁺)

Example 20

3-[3-[N-(Benzoxazol-2-yl)-N-n-octyl]aminopropoxy]benzoic acid

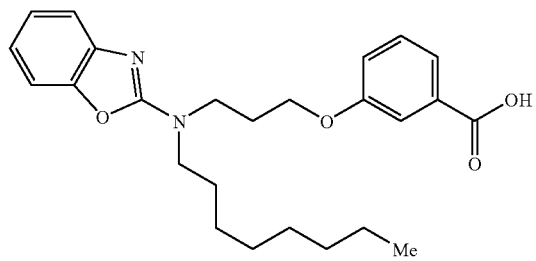

MS (m/z) 424 (M⁺)

Example 21

3-[3-[N-(Benzoxazol-2-yl)-N-n-propyl]aminopropoxy]benzoic acid

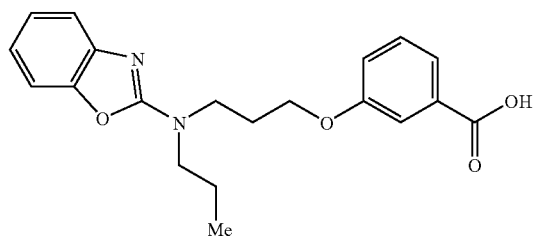

MS (m/z) 354 (M₊)

Example 22

3-[3-[N-(Benzoxazol-2-yl)-N-3-phenylpropyl]aminopropoxy]benzoic acid

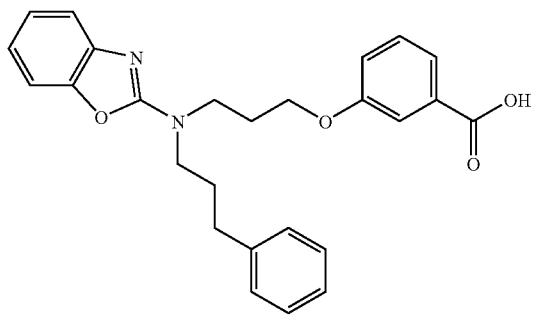

MS (m/z) 430 (M$^+$)

Example 23

2-[3-[N-(Benzoxazol-2-yl)-N-4-chlorobenzyl]aminopropoxy]benzoic acid

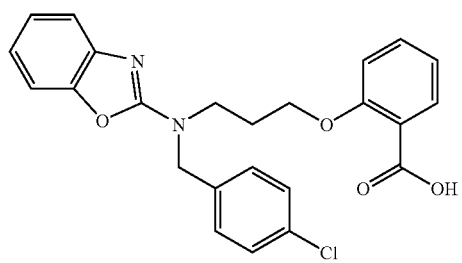

MS (m/z) 436 (M$^+$), 438 (M$^+$+2)

Example 24

2-[3-[N-(Benzoxazol-2-yl)-N-4-fluorobenzyl]aminopropoxy]benzoic acid

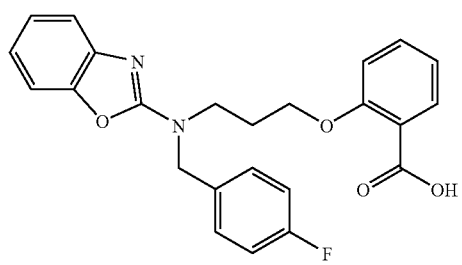

MS (m/z) 420 (M$^+$)

Example 25

2-[3-[N-(Benzoxazol-2-yl)-N-n-butyl]aminopropoxy]benzoic acid

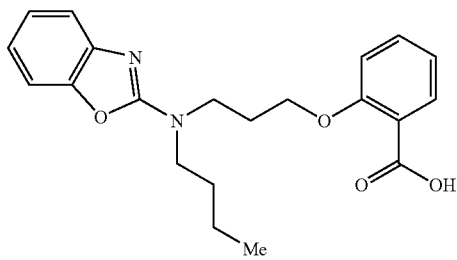

MS (m/z) 368 (M$^+$)

Example 26

2-[3-[N-(Benzoxazol-2-yl)-N-n-hexyl]aminopropoxy]benzoic acid

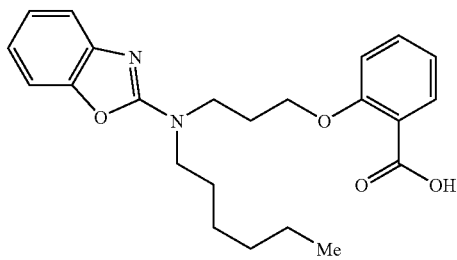

MS (m/z) 396 (M$^+$)

Example 27

2-[3-[N-(Benzoxazol-2-yl)-N-n-octyl]aminopropoxy]benzoic acid

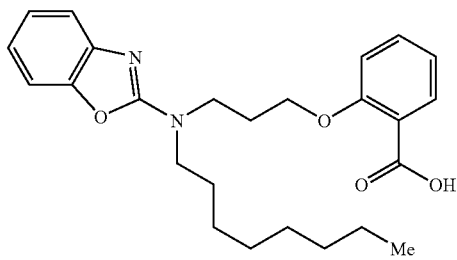

MS (m/z) 424 (M$^+$)

Example 28

2-[3-[N-(Benzoxazol-2-yl)-N-n-propyl]aminopropoxy]benzoic acid

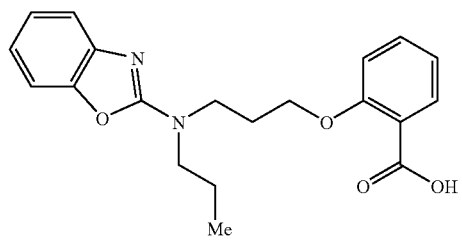

MS (m/z) 354 (M+)

Example 29

2-[3-[N-(Benzoxazol-2-yl)-N-3-phenylpropyl]aminopropoxy]benzoic acid

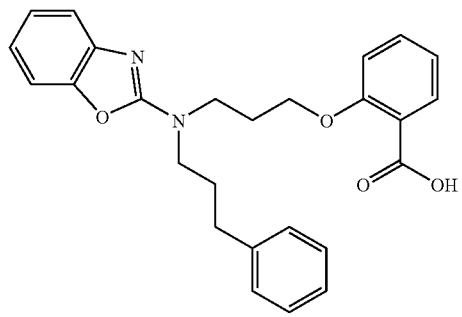

MS (m/z) 430 (M+)

Example 30

2-[3-[N-(Benzoxazol-2-yl)-N-2-phenoxyethyl]aminopropoxy]benzoic acid

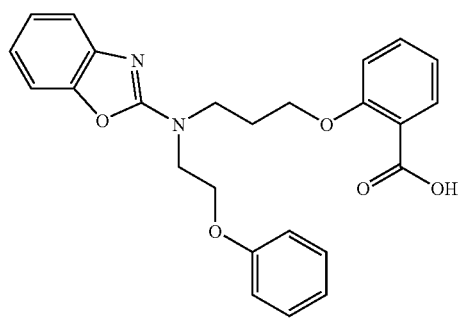

MS (m/z) 432 (M+)

Example 31

2-[3-[N-(Benzoxazol-2-yl)-N-3-phenoxypropyl]aminopropoxy]benzoic acid

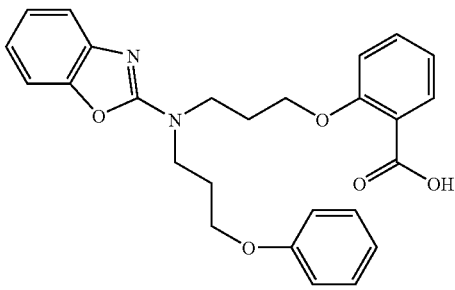

MS (m/z) 446 (M+)

Example 32

4-[3-[N-(Benzoxazol-2-yl)-N-4-chorobenzyl]aminopropoxy]benzoic acid

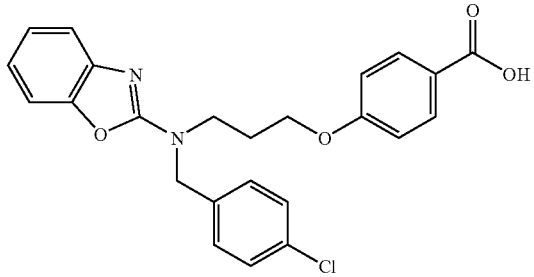

MS (m/z) 436 (M+), 438 (M++2)

Example 33

4-[3-[N-(Benzoxazol-2-yl)-N-2-(4-chorophenoxy)ethyl]aminopropoxy]benzoic acid

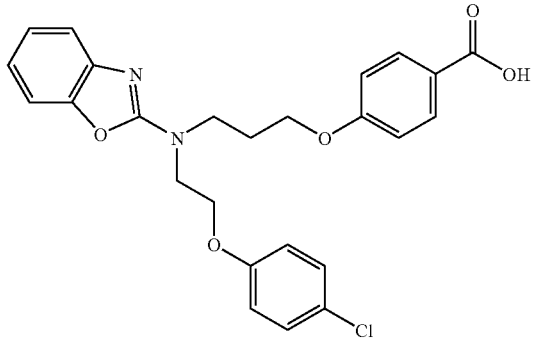

MS (m/z) 466 (M+), 468 (M++2)

Example 34

4-[3-[N-(Benzoxazol-2-yl)-N-ethyl]aminopropoxy]benzoic acid

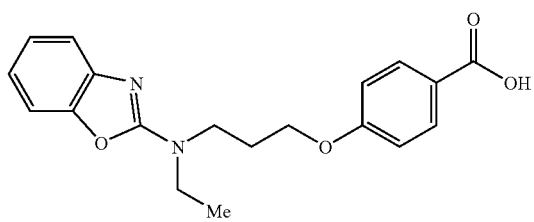

MS (m/z) 340 (M⁺)

Example 35

4-[3-[N-(Benzoxazol-2-yl)-N-methyl]aminopropoxy]benzoic acid

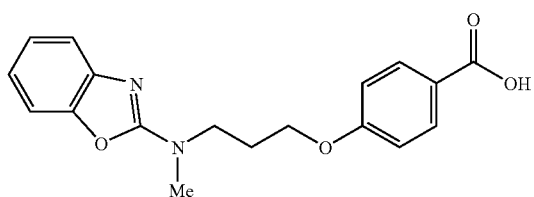

MS (m/z) 326 (M⁺)

Example 36

4-[3-[N-(Benzoxazol-2-yl)-N-n-butyl]aminopropoxy]benzoic acid

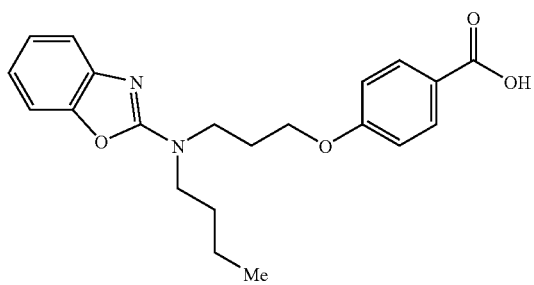

MS (m/z) 368 (M⁺)

Example 37

4-[3-[N-(Benzoxazol-2-yl)-N-n-heptyl]aminopropoxy]benzoic acid

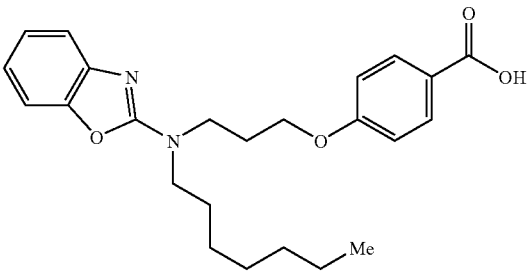

MS (m/z) 410 (M⁺)

Example 38

4-[3-[N-(Benzoxazol-2-yl)-N-n-hexyl]aminopropoxy]benzoic acid

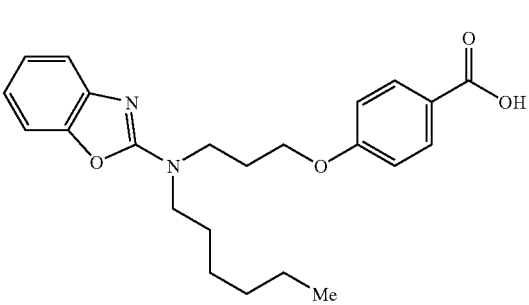

MS (m/z) 396 (M⁺)

Example 39

4-[3-[N-(Benzoxazol-2-yl)-N-n-octyl]aminopropoxy]benzoic acid

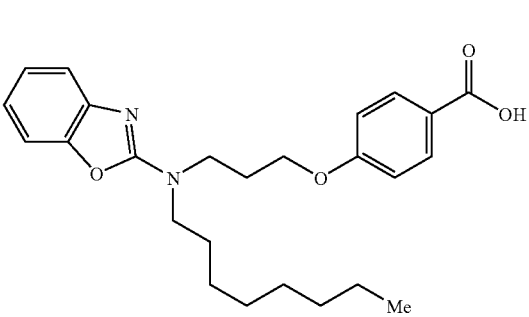

MS (m/z) 424 (M⁺)

Example 40

4-[3-[N-(Benzoxazol-2-yl)-N-n-propyl]aminopropoxy]benzoic acid

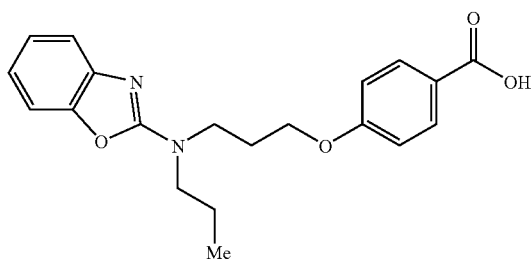

MS (m/z) 354 (M$^+$)

Example 41

4-[3-[N-(Benzoxazol-2-yl)-N-3-phenylpropyl]aminopropoxy]benzoic acid

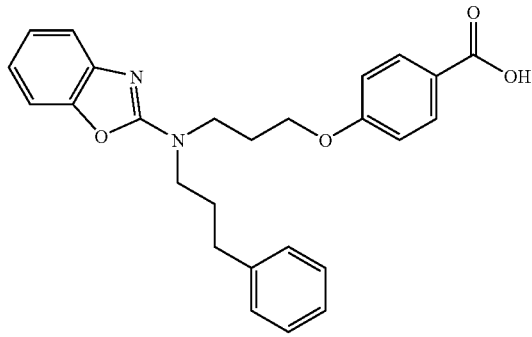

MS (m/z) 430 (M$^+$)

Example 42

4-[3-[N-(Benzoxazol-2-yl)-N-3-phenoxypropyl]aminopropoxy]benzoic acid

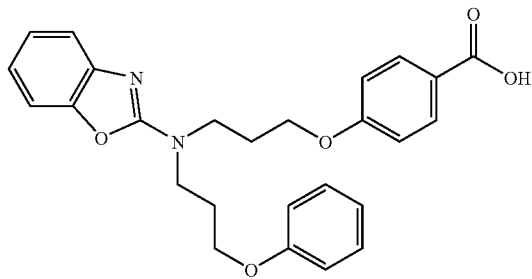

MS (m/z) 446 (M$^+$)

Example 43

3-[4-[N-(Benzoxazol-2-yl)-N-4-chlorobenzyl]aminobutoxy]benzoic acid

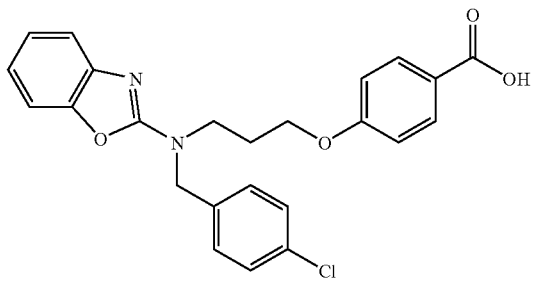

MS (m/z) 450 (M$^+$), 452 (M$^+$+2)

Example 44

3-[4-[N-(Benzoxazol-2-yl)-N-3-phenylpropyl]aminobutoxy]benzoic acid

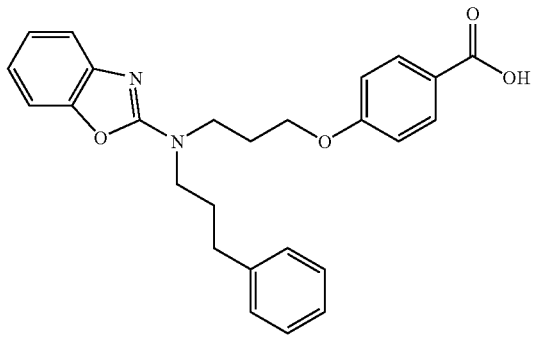

MS (m/z) 444 (M$^+$),

Example 45

3-[4-[N-(Benzoxazol-2-yl)-N-2-(4-chloropheoxyl)ethyl]aminobutoxy]benzoic acid

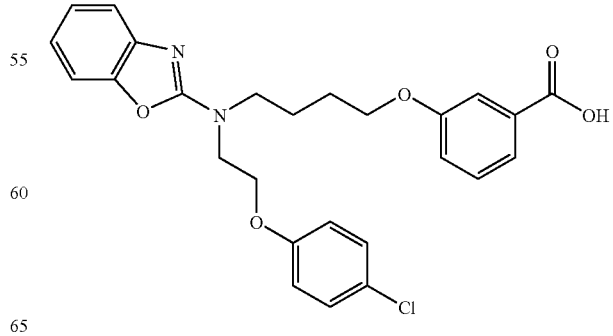

MS (m/z) 480 (M$^+$), 482 (M$^+$+2)

Example 46

3-[4-[N-(Benzoxazol-2-yl)-N-n-heptyl]aminobutoxy]benzoic acid

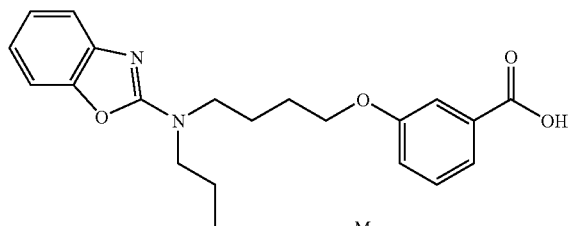

MS (m/z) 424 (M$^+$)

Example 47

3-[4-[N-(Benzoxazol-2-yl)-N-n-pentyl]aminobutoxy]benzoic acid

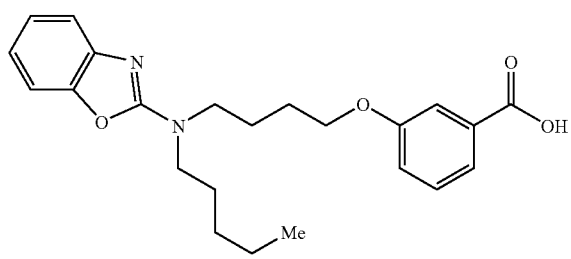

MS (m/z) 395 (M$^+$)

Example 48

3-[4-[N-(Benzoxazol-2-yl)-N-3-phenoxypropyl]aminobutoxy]benzoic acid

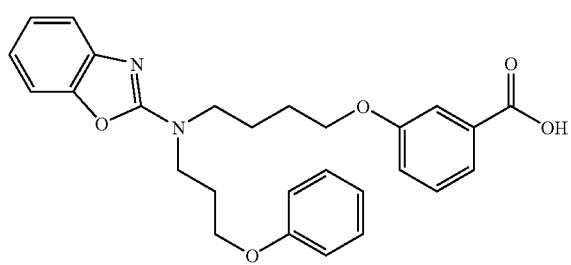

MS (m/z) 460 (M$^+$)

Example 49

2-[4-[N-(Benzoxazol-2-yl)-N-4-chlorobenzyl]aminobutoxy]benzoic acid

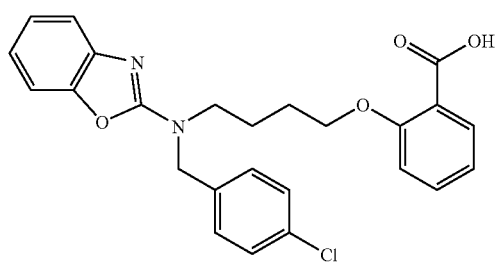

MS (m/z) 450 (M$^+$), 452 (M$^+$+2)

Example 50

2-[4-[N-(Benzoxazol-2-yl)-N-n-octyl]aminobutoxy]benzoic acid

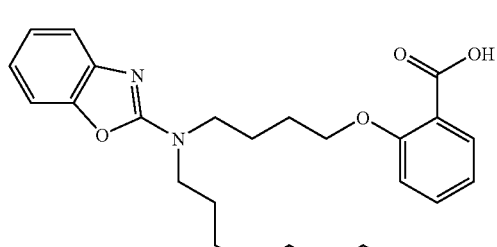

MS (m/z) 438 (M$^+$)

Example 51

2-[4-[N-(Benzoxazol-2-yl)-N-n-propyl]aminobutoxy]benzoic acid

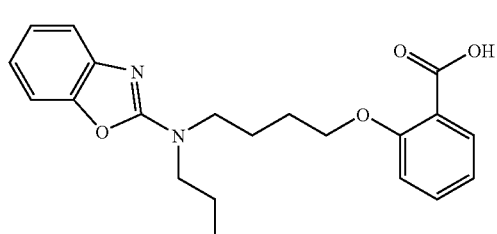

MS (m/z) 368 (M$^+$)

Example 52

2-[4-[N-(Benzoxazol-2-yl)-N-2-phenoxyethyl]aminobutoxy]benzoic acid

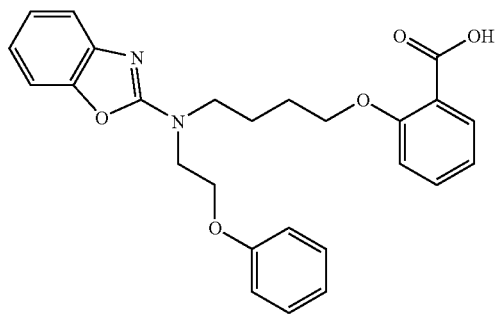

MS (m/z) 446 (M$^+$)

Example 53

2-[4-[N-(Benzoxazol-2-yl)-N-3-phenoxypropyl]aminobutoxy]benzoic acid

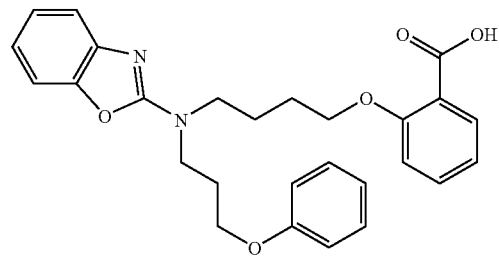

MS (m/z) 460 (M$^+$)

Example 54

4-[4-[N-(Benzoxazol-2-yl)-N-4-chlorobenzyl]aminobutoxy]benzoic acid

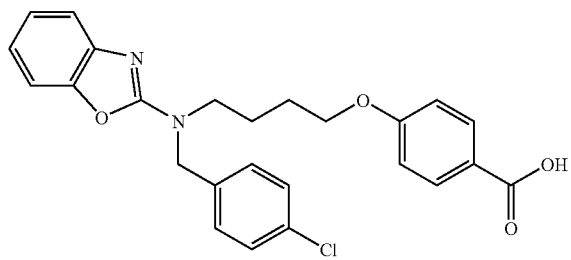

MS (m/z) 450 (M$^+$), 452 (M$^+$+2)

Example 55

4-[4-[N-(Benzoxazol-2-yl)-N-2-(4-chlorophenoxy)ethyl]aminobutoxy]benzoic acid

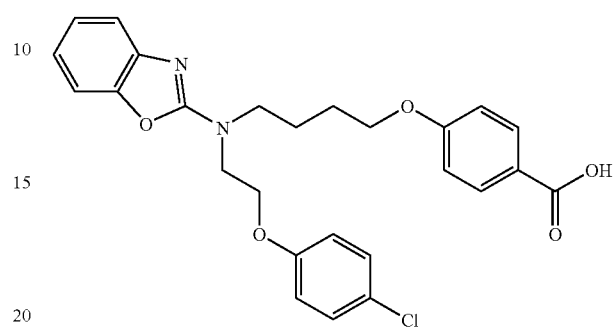

MS (m/z) 480 (M$^+$), 482 (M$^+$+2)

Example 56

4-[4-[N-(Benzoxazol-2-yl)-N-ethyl]aminobutoxy]benzoic acid

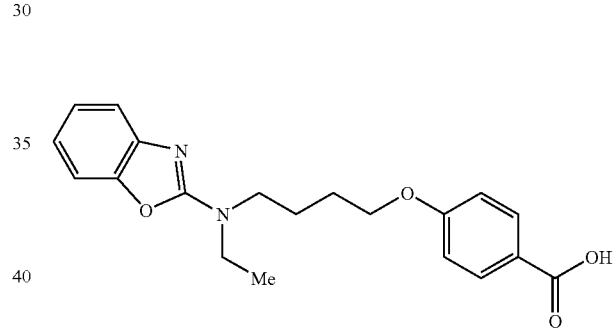

MS (m/z) 354 (M$^+$)

Example 57

4-[4-[N-(Benzoxazol-2-yl)-N-methyl]aminobutoxy]benzoic acid

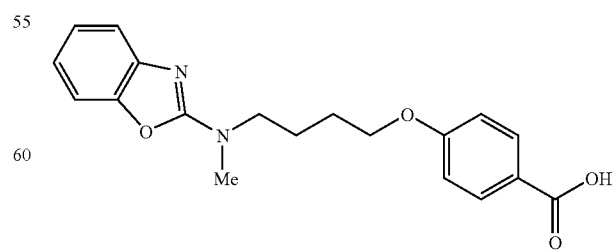

MS (m/z) 340 (M$^+$)

Example 58

4-[4-[N-(Benzoxazol-2-yl)-N-n-butyl]aminobutoxy]benzoic acid

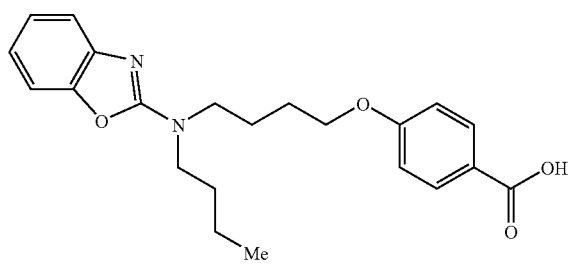

MS (m/z) 382 (M⁺)

Example 59

4-[4-[N-(Benzoxazol-2-yl)-N-n-heptyl]aminobutoxy]benzoic acid

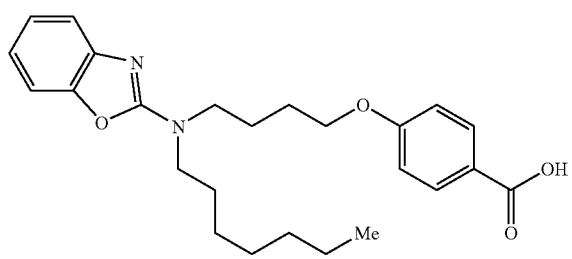

MS (m/z) 424 (M⁺)

Example 60

4-[4-[N-(Benzoxazol-2-yl)-N-n-hexyl]aminobutoxy]benzoic acid

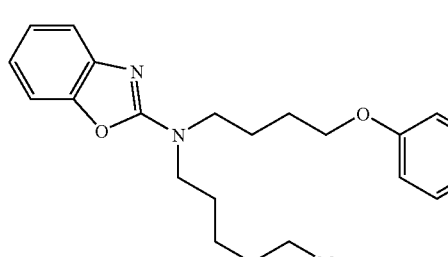

MS (m/z) 410 (M⁺)

Example 61

4-[4-[N-(Benzoxazol-2-yl)-N-n-octyl]aminobutoxy]benzoic acid

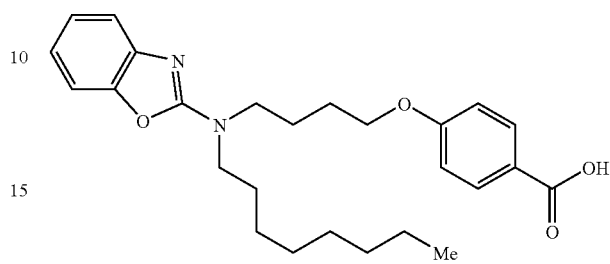

MS (m/z) 438 (M⁺)

Example 62

4-[4-[N-(Benzoxazol-2-yl)-N-n-propyl]aminobutoxy]benzoic acid

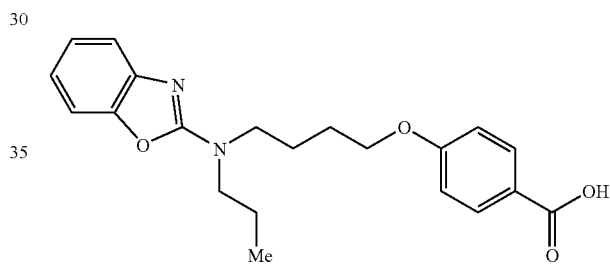

MS (m/z) 368 (M⁺)

Example 63

4-[4-[N-(Benzoxazol-2-yl)-N-3-phenylpropyl]aminobutoxy]benzoic acid

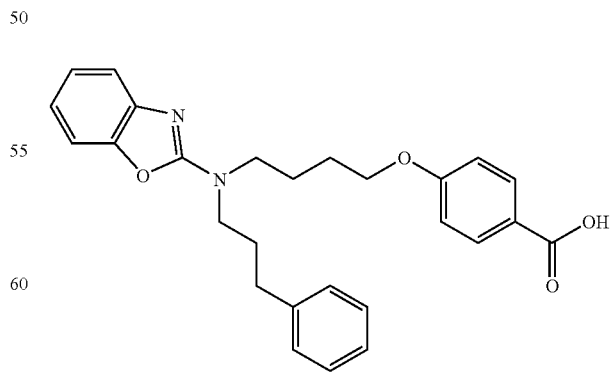

MS (m/z) 444 (M⁺)

Example 64

4-[4-[N-(Benzoxazol-2-yl)-N-3-phenoxypropyl]aminobutoxy]benzoic acid

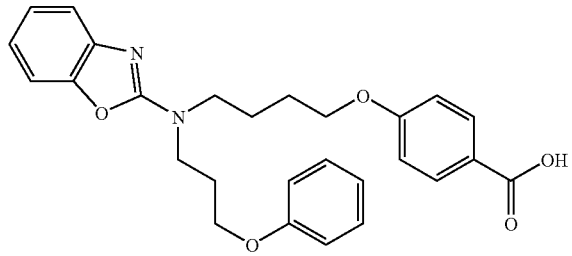

MS (m/z) 460 (M+)

Example 65

2-[3-[N-(Benzoxazol-2-yl)-N-2-phenoxyethyl]aminopropylthio]benzoic acid

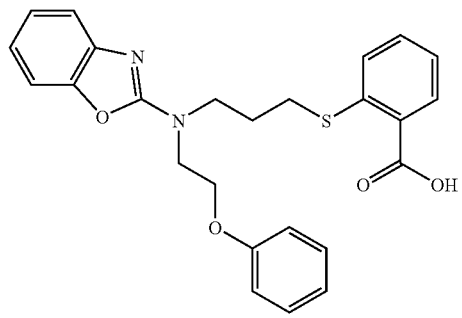

$^1$H-NMR (400 MHz, CDCl$_3$) δ:
2.21 (quintet, J=7 Hz, 2H), 3.03 (t, J=7 Hz, 2H), 3.87 (t, J=7 Hz, 2H), 3.96 (t, J=5 Hz, 2H), 4.25 (t, J=5 Hz, 2H), 6.85 (d, J=8 Hz, 2H), 6.92 (t, J=7 Hz, 1H), 7.01 (t, J=8 Hz, 1H), 7.14-7.26 (m, 5H), 7.30 (d, J=7 Hz, 1H), 7.37-7.43 (m, 2H), 8.07 (d, J=8 Hz, 1H)

Example 66

2-[4-[N-(Benzoxazol-2-yl)-N-ethyl]aminobutylthio]benzoic acid

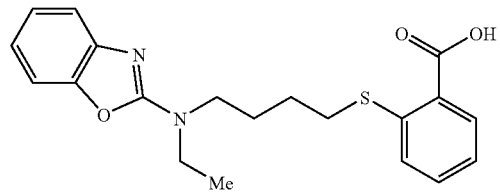

$^1$H-NMR (400 MHz, DMSO-d$_6$) δ:
1.20 (t, J=7 Hz, 3H), 1.66 (tt, J=7, 7 Hz, 2H), 1.81 (tt, J=7, 7 Hz, 2H), 2.99 (t, J=7 Hz, 2H), 3.50-3.55 (m, 4H), 6.97 (t, J=8 Hz, 1H), 7.12 (t, J=8 Hz, 1H), 7.19 (t, J=7 Hz, 1H), 7.25 (d, J=8 Hz, 1H), 7.36-7.47 (m, 3H), 7.84 (d, J=8 Hz, 1H), 13.0 (s, 1H)

Example 67

2-[4-[N-(Benzoxazol-2-yl)-N-methyl]aminobutylthio]benzoic acid

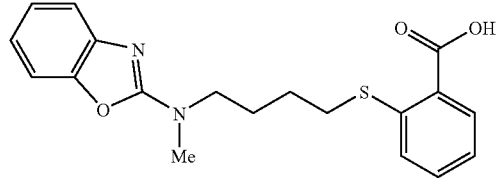

$^1$H NMR (400 MHz, DMSO-d$_6$) δ:
1.65 (tt, J=8, 7 Hz, 2H), 1.80 (tt, J=8, 7 Hz, 2H), 2.98 (t, J=7 Hz, 2H), 3.11 (s, 3H), 3.55 (t, J=7 Hz, 2H), 6.97 (td, J=8, 1 Hz, 1H), 7.12 (td, J=8, 1 Hz, 1H), 7.18 (t, J=8 Hz, 1H), 7.25 (d, J=7 Hz, 1H), 7.38 (t, J=8 Hz, 2H), 7.46 (td, J=8, 2 Hz, 1H), 7.84 (d, J=8 Hz, 1H), 13.0 (s, 1H)

Example 68

2-[4-[N-(Benzoxazol-2-yl)-N-n-propyl]aminobutylthio]benzoic acid

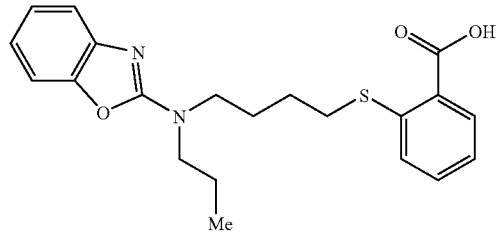

$^1$H-NMR (400 MHz, CDCl$_3$) δ:
0.95 (t, J=7 Hz, 3H), 1.64-1.78 (m, 4H), 1.80-1.95 (m, 2H), 2.92 (t, J=7 Hz, 2H), 3.45 (t, J=8 Hz, 2H), 3.53 (t, J=8 Hz, 2H), 6.99 (t, J=7 Hz, 1H), 7.13-7.17 (m, 2H), 7.23 (d, J=8 Hz, 1H), 7.30-7.37 (m, 2H), 7.46 (d, J=8 Hz, 1H), 7.98 (d, J=7 Hz, 1H)

Example 69

2-[5-[N-(Benzoxazol-2-yl)-N-cyclohexylmethyl]aminopentylthio]benzoic acid

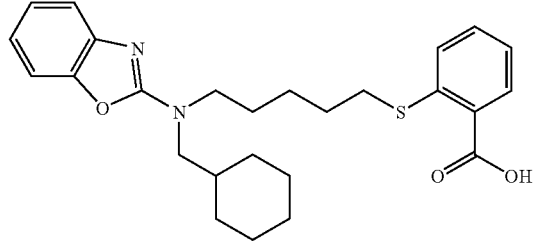

$^1$H-NMR (400 MHz, CDCl$_3$) δ:
0.98-1.03 (m, 2H), 1.15-1.24 (m, 3H), 1.51-1.55 (m, 2H), 1.71-1.78 (m, 10H), 2.84 (t, J=7 Hz, 2H), 3.35 (d, J=7 Hz, 2H), 3.52 (t, J=8 Hz, 2H), 6.99 (dt, J=8, 1 Hz, 1H), 7.14 (dt, J=8, 1 Hz, 1H), 7.19 (d, J=8 Hz, 1H), 7.24 (d, J=8 Hz, 1H), 7.28 (d, J=8 Hz, 1H), 7.38-7.42 (m, 2H), 8.07 (dd, J=8, 1 Hz, 1H).

Example 70

2-[5-[N-(Benzoxazol-2-yl)-N-isopropyl]aminopentylthio]benzoic acid

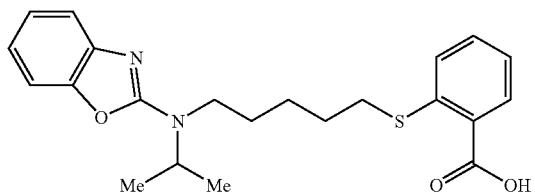

¹H-NMR (400 MHz, CDCl₃) δ:
1.30 (d, J=7 Hz, 6H), 1.54 (tt, J=8, 7 Hz, 2H), 1.77 (quintet, J=8 Hz, 4H), 2.86 (t, J=7 Hz, 2H), 3.41 (t, J=8 Hz, 2H), 4.47 (septet, J=7 Hz, 1H), 6.99 (td, J=8, 1 Hz, 1H), 7.14 (td, J=8, 1 Hz, 1H), 7.19 (t, J=8 Hz, 1H), 7.23-7.30 (m, 2H), 7.39-7.43 (m, 2H), 8.08 (dd, J=8, 2 Hz, 1H).

Example 71

2-[5-[N-(Benzoxazol-2-yl)-N-n-butyl]aminopentylthio]benzoic acid

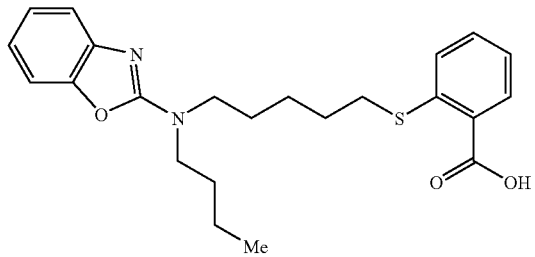

¹H-NMR (270 MHz, CDCl₃) δ:
0.96 (t, J=7 Hz, 3H), 1.38-1.85 (m, 10H), 2.87 (t, J=7 Hz, 2H), 3.45-3.62 (m, 4H), 6.99 (t, J=8 Hz, 1H), 7.11-7.34 (m, 6H), 8.08 (dd, J=8, 1 Hz, 1H).

Example 72

2-[5-[N-(Benzoxazol-2-yl)-N-n-pentyl]aminopentylthio]benzoic acid

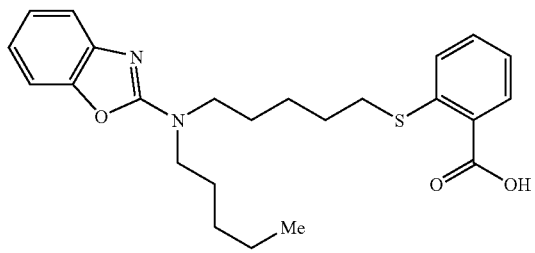

¹H-NMR (CDCl₃) δ:
0.89 (t, J=7 Hz, 3H), 1.25-1.48 (m, 8H), 1.64 (q, J=7 Hz, 4H), 2.80 (br, 2H), 3.45 (t, J=7 Hz, 4H), 6.96 (t, J=8 Hz, 1H), 7.11 (m, 1H), 7.12 (t, J=8 Hz, 1H), 7.21-7.26 (m, 2H), 7.31 (m, 1H), 7.36 (d, J=8 Hz, 1H), 7.99 (d, J=8 Hz, 1H)

Example 73

2-[2-[N-(Benzoxazol-2-yl)-N-(2-methyl-3-nitrobenzyl)]aminoethylthio]benzoic acid

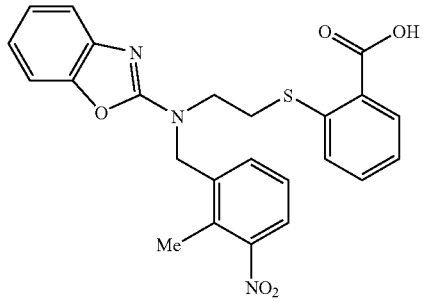

MS (m/z) 463 (M⁺)

Example 74

2-[2-[N-(Benzoxazol-2-yl)-N-2-nitrobenzyl]aminoethylthio]benzoic acid

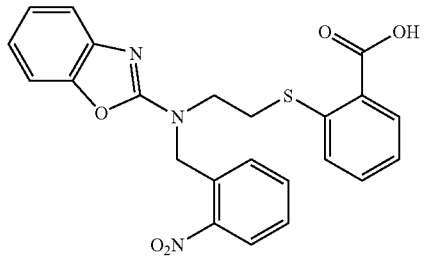

MS (m/z) 449 (M⁺)

Example 75

2-[2-[N-(Benzoxazol-2-yl)-N-4-chlorobenzyl]aminoethylthio]benzoic acid

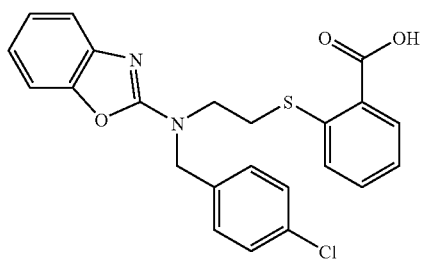

MS (m/z) 438 (M⁺), 440 (M⁺+2)

Example 76

2-[2-[N-(Benzoxazol-2-yl)-N-n-butyl]aminoethylthio]benzoic acid

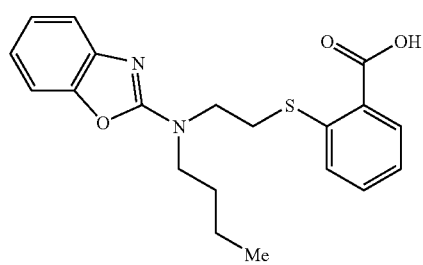

MS (m/z) 370 (M⁺)

Example 77

2-[2-[N-(Benzoxazol-2-yl)-N-n-heptyl]aminoethylthio]benzoic acid

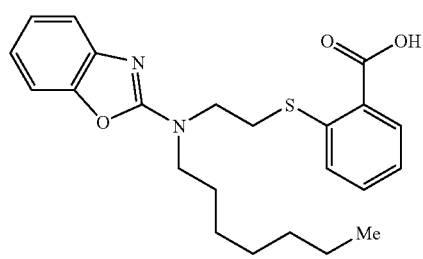

MS (m/z) 412 (M⁺)

Example 78

2-[2-[N-(Benzoxazol-2-yl)-N-n-octyl]aminoethylthio]benzoic acid

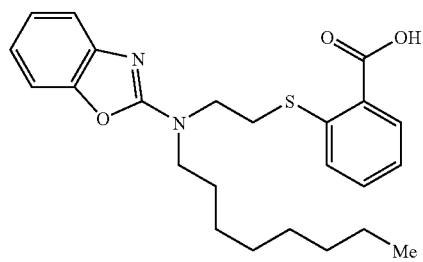

MS (m/z) 426 (M⁺)

Example 79

2-[2-[N-(Benzoxazol-2-yl)-N-3-phenylpropyl]aminoethylthio]benzoic acid

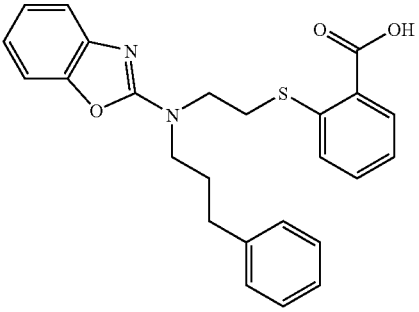

MS (m/z) 432 (M⁺)

Example 80

2-[2-[N-(Benzoxazol-2-yl)-N-3-phenoxypropyl]aminoethylthio]benzoic acid

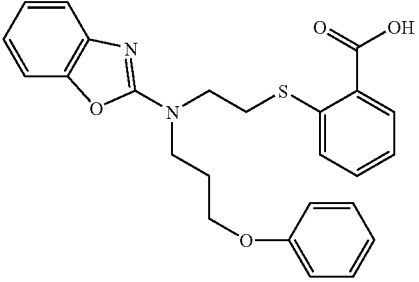

MS (m/z) 448 (M⁺)

Example 81

2-[3-[N-(Benzoxazol-2-yl)-N-4-chlorobenzyl]aminopropylthio]benzoic acid

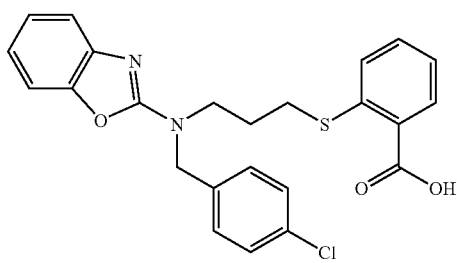

MS (m/z) 453 (M⁺), 455 (M⁺+2)

Example 82

2-[3-[N-(Benzoxazol-2-yl)-N-ethyl]aminopropylthio]benzoic acid

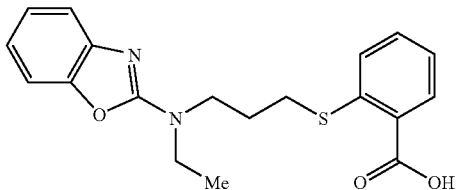

MS (m/z) 356 (M$^+$)

Example 83

2-[3-[N-(Benzoxazol-2-yl)-N-isopropyl]aminopropylthio]benzoic acid

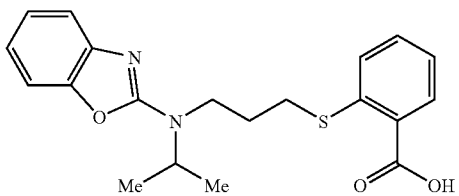

MS (m/z) 370 (M$^+$)

Example 84

2-[3-[N-(Benzoxazol-2-yl)-N-n-butyl]aminopropylthio]benzoic acid

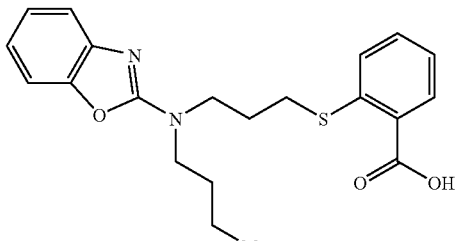

MS (m/z) 385 (M$^+$)

Example 85

2-[3-[N-(Benzoxazol-2-yl)-N-n-hexyl]aminopropylthio]benzoic acid

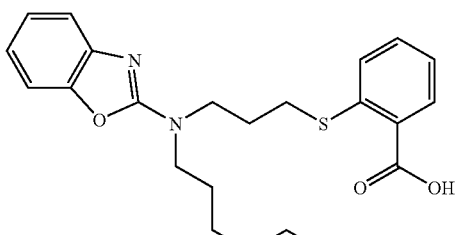

MS (m/z) 413 (M$^+$)

Example 86

2-[3-[N-(Benzoxazol-2-yl)-N-n-octyl]aminopropylthio]benzoic acid

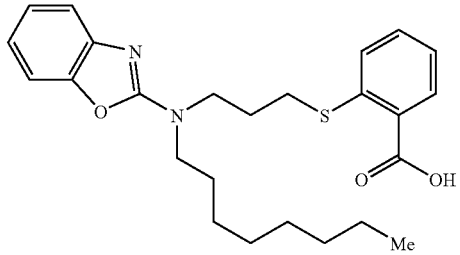

MS (m/z) 441 (M$^+$)

Example 87

2-[3-[N-(Benzoxazol-2-yl)-N-n-pentyl]aminopropylthio]benzoic acid

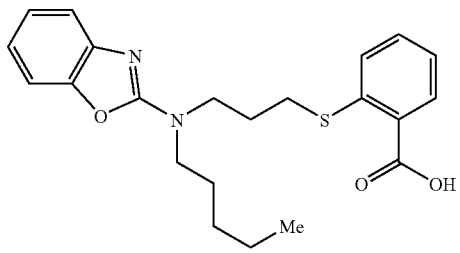

MS (m/z) 398 (M$^+$)

Example 88

2-[3-[N-(Benzoxazol-2-yl)-N-n-propyl]aminopropylthio]benzoic acid

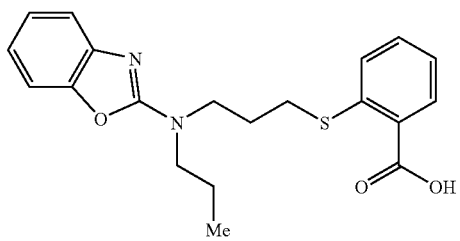

MS (m/z) 370 (M$^+$)

Example 89

2-[3-[N-(Benzoxazol-2-yl)-N-3-phenylpropyl]aminopropylthio]benzoic acid

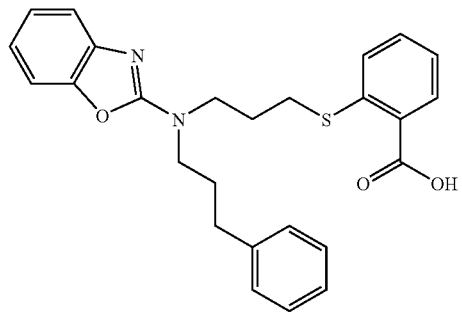

MS (m/z) 447 (M$^+$)

Example 90

2-[4-[N-(Benzoxazol-2-yl)-N-4-chlorobenzyl]aminobutylthio]benzoic acid

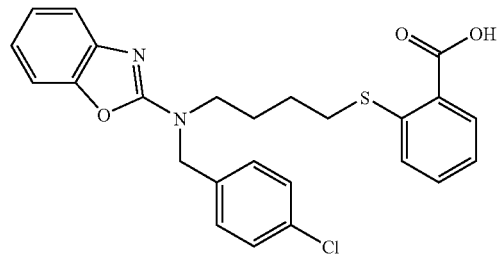

MS (m/z) 467 (M$^+$), 469 (M$^+$+2)

Example 91

2-[4-[N-(Benzoxazol-2-yl)-N-cyclohexylmethyl]aminobutylthio]benzoic acid

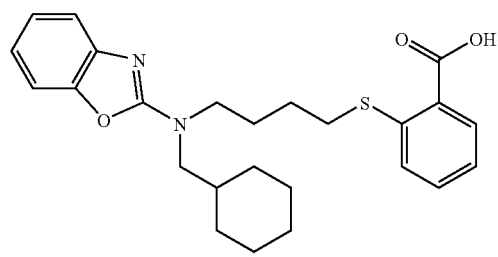

MS (m/z) 439 (M$^+$)

Example 92

2-[4-[N-(Benzoxazol-2-yl)-N-n-butyl]aminobutylthio]benzoic acid

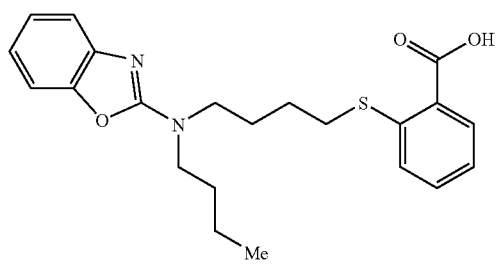

MS (m/z) 399 (M$^+$)

Example 93

2-[4-[N-(Benzoxazol-2-yl)-N-n-hexyl]aminobutylthio]benzoic acid

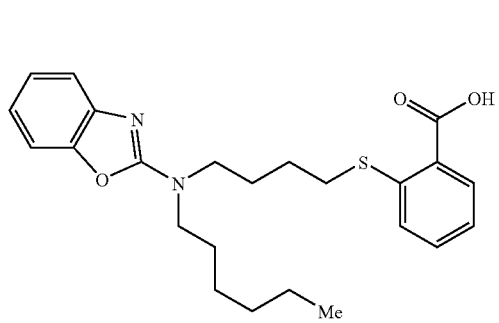

MS (m/z) 427 (M$^+$)

Example 94

2-[4-[N-(Benzoxazol-2-yl)-N-n-octyl]aminobutylthio]benzoic acid

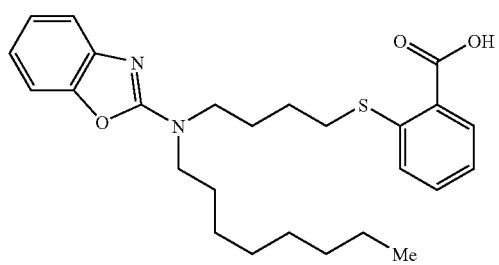

MS (m/z) 455 (M$^+$)

Example 95

2-[4-[N-(Benzoxazol-2-yl)-N-n-pentyl]aminobutylthio]benzoic acid

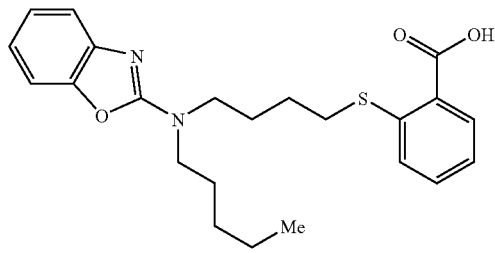

MS (m/z) 413 (M+)

Example 96

2-[4-[N-(Benzoxazol-2-yl)-N-benzyl]aminobutylthio]benzoic acid

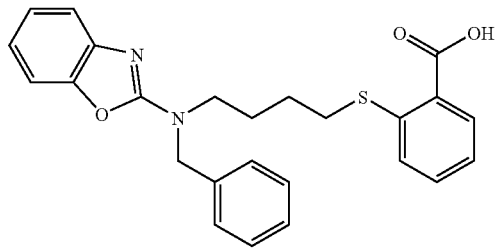

MS (m/z) 433 (M+)

Example 97

2-[4-[N-(Benzoxazol-2-yl)-N-3-phenylpropyl]aminobutylthio]benzoic acid

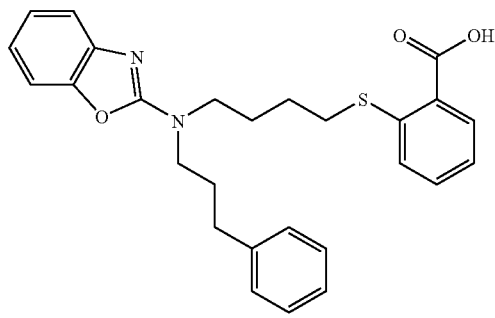

MS (m/z) 461 (M+)

Example 98

2-[5-[N-(Benzoxazol-2-yl)-N-4-chlorobenzyl]aminopentylthio]benzoic acid

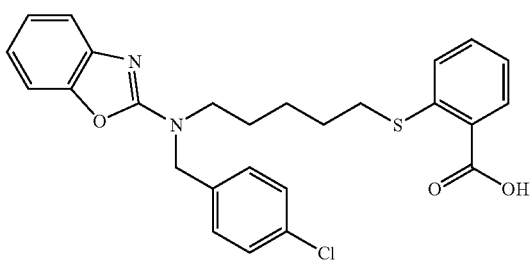

MS (m/z) 480 (M+), 482 (M++2)

Example 99

2-[5-[N-(Benzoxazol-2-yl)-N-ethyl]aminopentylthio]benzoic acid

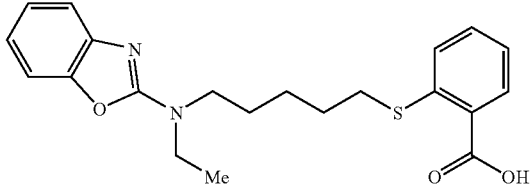

MS (m/z) 384 (M+)

Example 100

2-[5-[N-(Benzoxazol-2-yl)-N-methyl]aminopentylthio]benzoic acid

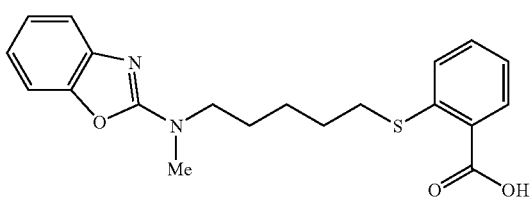

MS (m/z) 370 (M+)

Example 101

2-[5-[N-(Benzoxazol-2-yl)-N-n-hexyl]aminopentylthio]benzoic acid

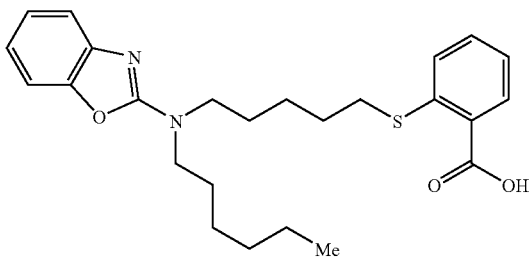

MS (m/z) 438 (M+)

Example 102

2-[5-[N-(Benzoxazol-2-yl)-N-n-octyl]aminopentylthio]benzoic acid

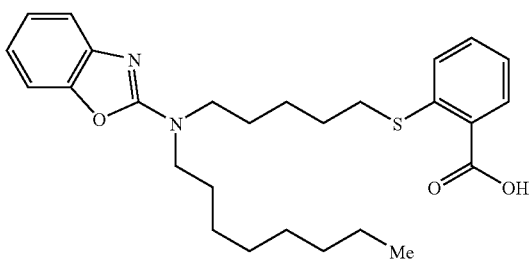

MS (m/z) 468 (M+)

Example 103

2-[5-[N-(Benzoxazol-2-yl)-N-n-propyl]aminopentylthio]benzoic acid

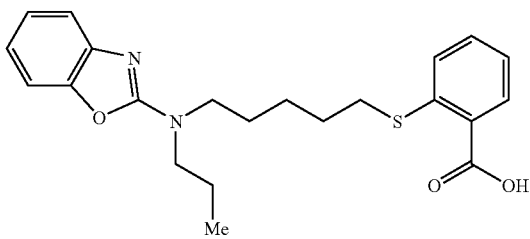

MS (m/z) 398 (M+)

Example 104

2-[5-[N-(Benzoxazol-2-yl)-N-3-phenylpropyl]aminopentylthio]benzoic acid

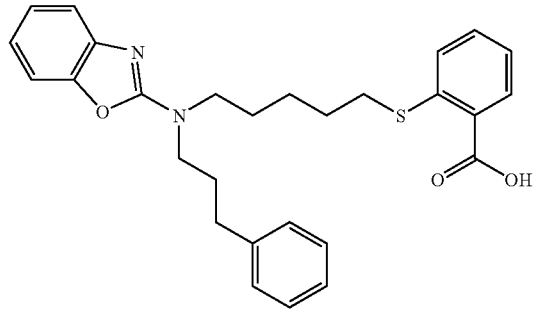

MS (m/z) 474 (M+)

Example 105

2-[5-[N-(Benzoxazol-2-yl)-N-3-phenoxypropyl]aminopentylthio]benzoic acid

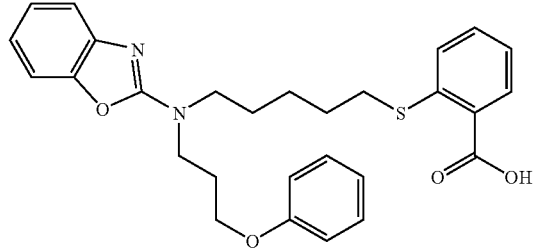

MS (m/z) 490 (M+)

Example 106

2-[6-[N-(Benzoxazol-2-yl)-N-4-chlorobenzyl]aminohexylthio]benzoic acid

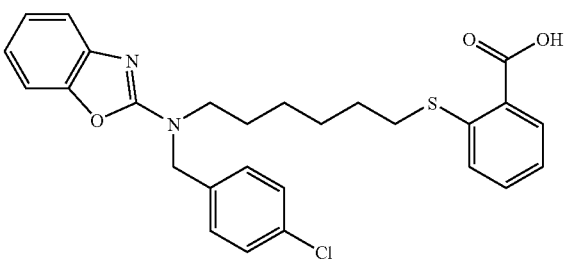

MS (m/z) 494 (M+), 496 (M++2)

Example 107

2-[4-[N-(Benzothiazol-2-yl)-N-3-(4-chlorophenoxy)propyl]aminobutylthio]benzoic acid

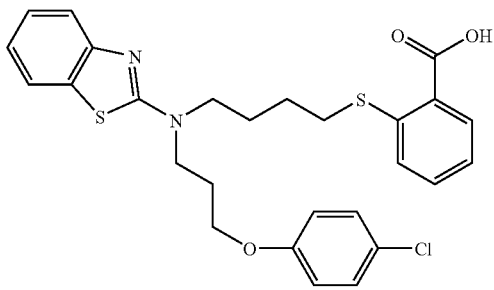

MS (m/z) 526 (M$^+$), 528 (M$^+$+2)

Example 108

2-[4-[N-(Benzothiazol-2-yl)-N-ethyl]aminobutylthio]benzoic acid

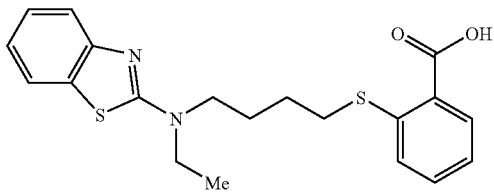

MS (m/z) 386 (M$^+$)

Example 109

2-[4-[N-(Benzothiazol-2-yl)-N-methyl]aminobutylthio]benzoic acid

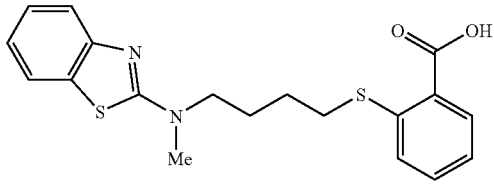

MS (m/z) 372 (M$^+$)

Example 110

2-[4-[N-(Benzothiazol-2-yl)-N-n-propyl]aminobutylthio]benzoic acid

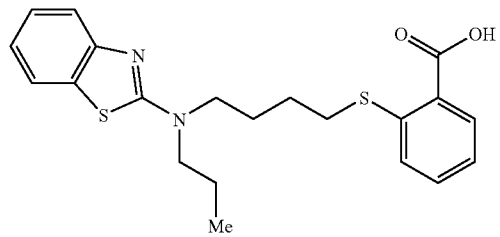

MS (m/z) 400 (M$^+$)

Example 111

2-[4-[N-(Benzothiazol-2-yl)-N-2-phenoxyethyl]aminobutylthio]benzoic acid

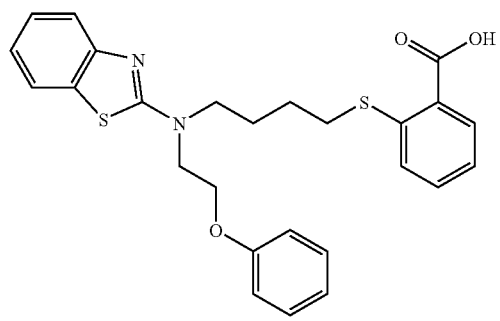

MS (m/z) 478 (M$^+$)

Example 112

Synthesis of 2-[5-[N-(Benzoxazol-2-yl)-N-n-pentyl]aminopentylsulfonyl]benzoic acid

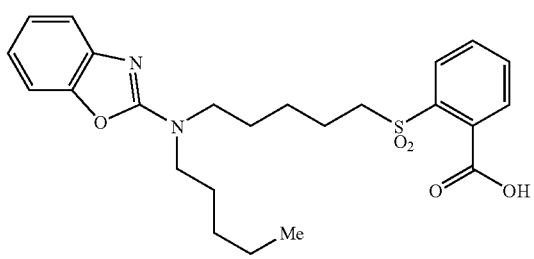

2-[5-[N-(Benzoxazol-2-yl)-N-n-pentyl]aminopentylthio]benzoic acid (34 mg, 0.08 mmol) obtained in Example 72 was dissolved in 10 mL of dichloromethane and reacted with m-chloroperbenzoic acid (57 mg, 0.33 mmol) at 0° C. The resulting mixture was stirred at the same temperature for 2 hours and further stirred at room temperature. After the completion of the reaction, the resulting mixture was diluted with a sodium thiosulfate solution and subsequently with a methanol solution and extracted with chloroform. The organic layer was dried with sodium sulfate and then concentrated under reduced pressure, followed by purification by silica gel column chromatography (chloroform:methanol=10:1) to give a compound of interest (28 mg, 75.9%).

$^1$H-NMR (270 MHz, CD$_3$OD) δ:

0.90 (t, J=7 Hz, 3H), 1.15-1.44 (m, 6H), 1.62-1.74 (m, 6H), 3.44 (t, J=7 Hz, 4H), 3.66 (t, J=8 Hz, 2H), 6.97 (t, J=8 Hz, 1H), 7.11 (t, J=8 Hz, 1H), 7.21-7.34 (m, 2H), 7.39-7.51 (m, 1H), 7.62 (d, J=3 Hz, 2H), 7.92 (d, J=8 Hz, 1H)

MS (m/z) 459(M$^+$)

Hereinafter, compounds of Examples 113 to 125 were synthesized in the same way as in Example 112.

Example 113

2-[2-[N-(Benzoxazol-2-yl)-N-n-butyl]aminoethylsulfonyl]benzoic acid

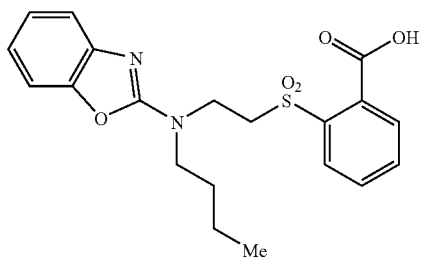

MS (m/z) 402 (M$^+$)

Example 114

2-[2-[N-(Benzoxazol-2-yl)-N-n-heptyl]aminoethylsulfonyl]benzoic acid

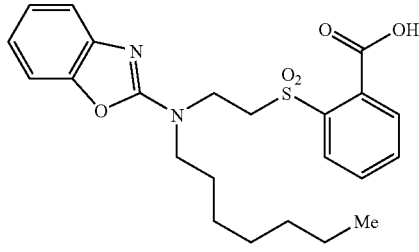

MS (m/z) 444 (M$^+$)

Example 115

2-[2-[N-(Benzoxazol-2-yl)-N-n-octyl]aminoethylsulfonyl]benzoic acid

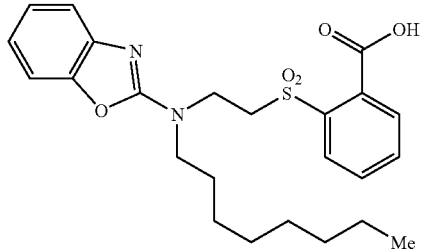

MS (m/z) 458 (M$^+$)

Example 116

2-[2-[N-(Benzoxazol-2-yl)-N-3-phenylpropyl]aminoethylsulfonyl]benzoic acid

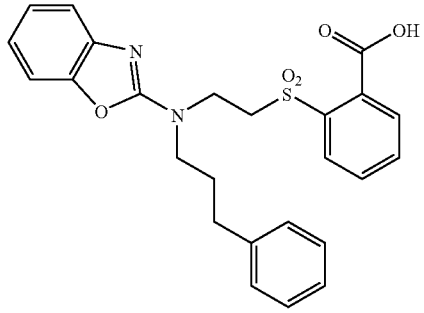

MS (m/z) 464 (M$^+$)

Example 117

2-[2-[N-(Benzoxazol-2-yl)-N-3-phenoxypropyl]aminoethylsulfonyl]benzoic acid

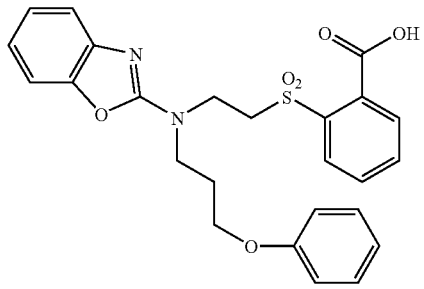

MS (m/z) 480 (M$^+$)

Example 118

2-[5-[N-(Benzoxazol-2-yl)-N-4-chlorobenzyl]amino-pentylsulfonyl]benzoic acid

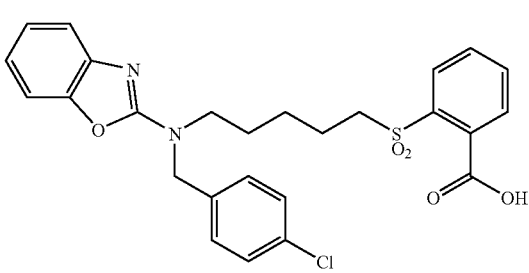

MS (m/z) 513 (M$^+$), 515 (M$^+$+2)

Example 119

2-[5-[N-(Benzoxazol-2-yl)-N-cyclohexylmethyl]aminopentylsulfonyl]benzoic acid

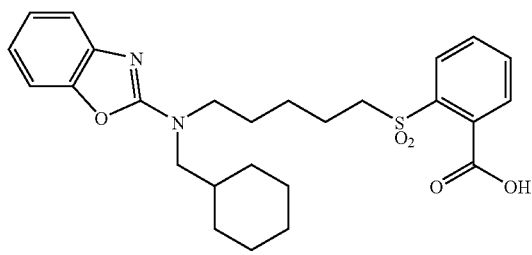

MS (m/z) 485 (M$^+$)

Example 120

2-[5-[N-(Benzoxazol-2-yl)-N-n-butyl]aminopentyl-sulfonyl]benzoic acid

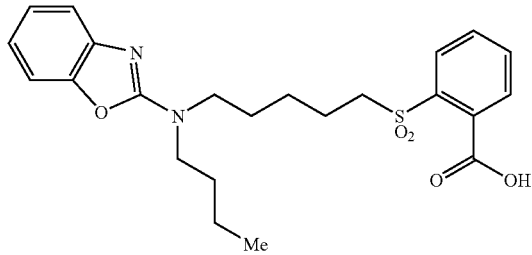

MS (m/z) 445 (M$^+$)

Example 121

2-[2-[N-(Benzoxazol-2-yl)-N-4-chlorobenzyl]amino-ethylsulfonyl]benzoic acid

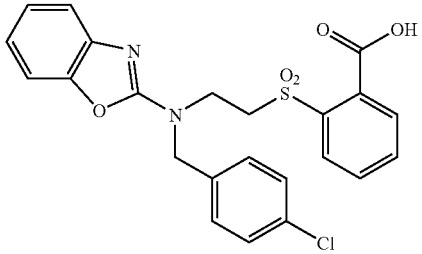

MS (m/z) 470 (M$^+$), 472 (M$^+$+2)

Example 122

2-[5-[N-(Benzoxazol-2-yl)-N-n-octyl]aminopentyl-sulfonyl]benzoic acid

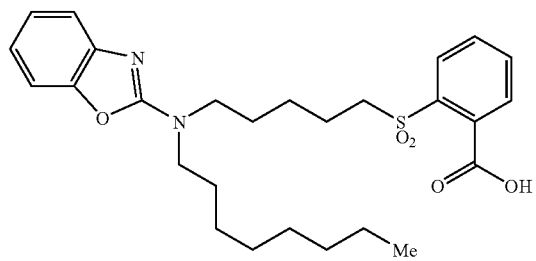

$^1$H-NMR (270 MHz, CD$_3$OD) δ:
0.77 (t, J=7 Hz, 3H), 1.18-1.38 (m, 12H), 1.53-1.70 (m, 6H), 3.35 (t, J=7 Hz, 4H), 3.57 (t, J=8 Hz, 2H), 6.89 (t, J=8 Hz, 1H), 7.03 (t, J=8 Hz, 1H), 7.15 (t, J=8 Hz, 2H), 7.35-7.44 (m, 1H), 7.76 (d, J=4 Hz, 2H), 7.82 (d, J=8 Hz, 1H)
MS (m/z) 501 (M$^+$)

Example 123

2-[5-[N-(Benzoxazol-2-yl)-N-n-propyl]aminopentyl-sulfonyl]benzoic acid

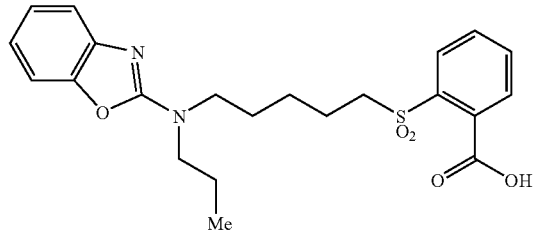

$^1$H-NMR (270 MHz, CD$_3$OD) δ:
0.93 (t, J=7 Hz, 3H), 1.14-1.26 (m, 2H), 1.63-1.74 (m, 6H), 3.43 (dd, J=14, 7 Hz, 4H), 3.56-3.68 (m, 2H), 6.97 (t, J=7 Hz, 1H), 7.11 (t, J=7 Hz, 1H), 7.23 (t, J=7 Hz, 2H), 7.47-7.51 (m, 1H), 7.61 (d, J=3 Hz, 2H), 7.91 (d, J=8 Hz, 1H)

Example 124

2-[5-[N-(Benzoxazol-2-yl)-N-3-phenylpropyl]aminopentylsulfonyl]benzoic acid

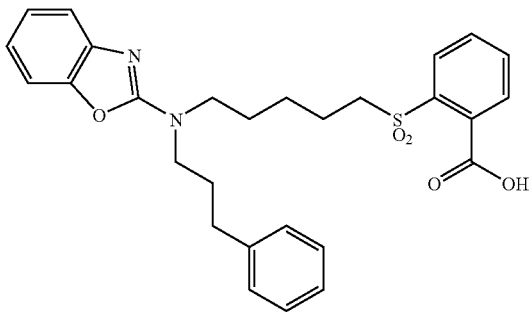

MS (m/z) 507 (M+)

Example 125

2-[5-[N-(Benzoxazol-2-yl)-N-3-phenoxypropyl]aminopentylsulfonyl]benzoic acid

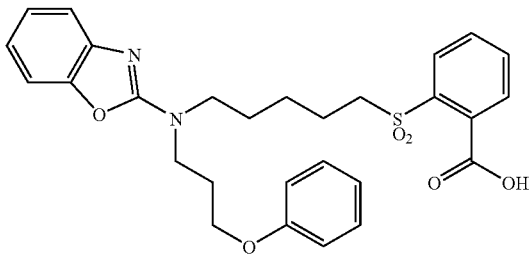

MS (m/z) 523 (M+)

Test Example 1

The PPAR receptor-activating effect of the compound of the present invention represented by the formula (1) was measured by a method described below (Proc. Natl. Acad. Sci., 92, pp 7297-7301, 1995; Journal of Lipid Research, 40, pp 2099-2110, 1999; and Proc. Natl. Acad. Sci, 98, pp 5306-5311, 2001).

(1) Measurement Method

Transfection Assay

All the transfection assays were conducted using African green monkey kidney-derived cell line COS cells. The COS cells were cultured at 5% $CO_2$ concentration using a DMEM medium containing 10% fetal bovine serum, glutamic acid, and an antibiotic as a culture solution.

Gal4-human PPARs chimeric constructs which were fused the DNA-binding region of yeast transcription factor Gal4 with the ligand-binding region of human PPARs were used as an expression vector. A chimera where 1st to 147th amino acids of the Gal4 transcription factor were fused with 166th to 467th amino acids of human PPARα, with 182nd to 505th amino acids of human PPARγ2, or with 137th to 441st amino acids of human PPARδ was used as the chimera for each isoform. A reporter vector used was firefly luciferase whose promoter region contains five Gal4 recognition sequences. The plasmids were transfected into the cells by a method using Lipofectamine. In addition, a β-galactosidase expression vector was used as an internal standard.

After the transfection into the cells, the medium was substituted with a DMEM medium (containing 0.2% serum) supplemented with the compound, in which the cells were then cultured for additional 16 hours. Thereafter, luciferase activity and β-galactosidase activity in the cell lysate were measured.

In the present experiment, dimethyl sulfoxide (DMSO) was used in the dissolution and dilution of the compound. When the cells were treated, the DMSO concentration in the DMEM medium (containing 0.2% serum) was adjusted to 0.1%. Positive compounds used were WY14643 for PPARα, rosiglitazone (Journal of Medicinal Chemistry, 43, pp 527-550, 2000) for PPARγ, and GW501516 (Proc. Natl. Acad. Sci, 98, pp 5306-5311, 2001) for PPARδ.

(2) Result

When luciferase activity at the addition of the positive compound for each isoform (PPARα: WY14643 10 μM, PPARγ: rosiglitazone 1 μM; and PPARδ: GW501516 1 μM) was given by 10.0, the relative activity of the compound of the present invention (added at 1 μM) was summarized in Table 1.

TABLE 1-1

| Example No. | hPPAR; Relative activity | | |
|---|---|---|---|
| | α | γ | δ |
| 6 | 17.3 | 1.2 | 0.3 |
| 13 | 15.2 | 6.2 | 0.1 |
| 19 | 15.1 | 1.7 | 0.5 |
| 20 | 21.7 | 1.5 | 0.2 |
| 27 | 13.7 | 1.9 | 0.1 |
| 45 | 12.3 | 3.5 | 0.6 |
| 46 | 16.5 | 1.9 | 0.3 |
| 47 | 10.4 | 1.2 | 0.3 |
| 48 | 16.0 | 2.1 | 0.2 |
| 50 | 13.3 | 2.9 | 0.1 |
| 52 | 13.8 | 2.1 | 0.1 |
| 53 | 16.0 | 3.5 | 0.1 |
| 60 | 11.9 | 1.8 | 0.1 |
| 70 | 12.4 | 1.4 | 0.2 |
| 71 | 11.0 | 2.0 | 0.5 |
| 72 | 13.5 | 1.7 | 0.6 |
| 73 | 11.2 | 1.1 | 0.2 |
| 74 | 10.2 | 0.7 | 0.3 |
| 77 | 18.9 | 2.0 | 0.2 |
| 78 | 20.8 | 2.1 | 0.2 |
| 79 | 13.3 | 1.1 | 0.2 |
| 80 | 17.8 | 1.6 | 0.2 |
| 93 | 12.3 | 4.1 | 0.4 |
| 94 | 12.0 | 3.5 | 1.4 |
| 97 | 11.6 | 4.6 | 0.2 |
| 98 | 14.7 | 3.3 | 0.7 |
| 99 | 16.8 | 2.2 | 0.3 |
| 100 | 20.2 | 1.7 | 0.2 |

TABLE 1-2

| Example No. | hPPAR; Relative activity | | |
|---|---|---|---|
| | α | γ | δ |
| 101 | 14.0 | 1.8 | 0.7 |
| 102 | 20.3 | 2.1 | 0.9 |
| 103 | 12.4 | 2.0 | 0.2 |
| 104 | 18.7 | 2.7 | 0.8 |

TABLE 1-2-continued

| Example No. | hPPAR; Relative activity | | |
|---|---|---|---|
| | α | γ | δ |
| 105 | 25.3 | 2.5 | 4.2 |
| 106 | 13.1 | 2.4 | 0.0 |
| 108 | 16.2 | 1.4 | 0.2 |
| 109 | 12.1 | 0.8 | 0.2 |
| 110 | 11.0 | 2.0 | 0.2 |
| 111 | 16.0 | 4.6 | 0.3 |
| 122 | 12.2 | 2.3 | 0.2 |
| WY14643 10 μM | 10.0 | — | — |
| Rosiglitazone 1 μM | — | 10.0 | — |
| GW501516 1 μM | — | — | 10.0 |

These results show that the compound of the present invention exhibits excellent hPPARα activation and selectivity. As described above, the compound of the present invention is an excellent hPPARα-selective activator.

What is claimed is:

1. A benzoic acid derivative represented by the following formula (1):

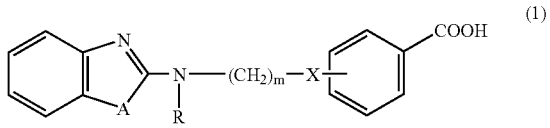

wherein A represents an oxygen atom;

R represents a hydrogen atom, a $C_{1-8}$ alkyl group, a $C_{3-8}$ alkenyl group, a $C_{3-8}$ alkynyl group, a $C_{3-7}$ cycloalkyl group, a $C_{3-7}$ cycloalkyl-$C_{1-8}$ alkyl group, a $C_{6-10}$ aryl group, a $C_{6-10}$ aryl-$C_{1-8}$ alkyl group (wherein the $C_{6-10}$ aryl moiety may be substituted with one or two groups selected from a halogen atom, a hydroxy group, a nitro group, an amino group, a di-$C_{1-4}$ alkylamino group, a $C_{1-4}$ alkyl group, a $C_{1-4}$ alkoxy group, a benzyloxy group, a phenylsulfonylmethyl group, and a $C_{1-4}$ alkanesulfonyloxy group), a $C_{6-10}$ aryl-oxy-$C_{1-8}$ alkyl group (wherein the $C_{6-10}$ aryl moiety may be substituted with one or two groups selected from a halogen atom, a hydroxy group, a nitro group, an amino group, a di-$C_{1-4}$ alkylamino group, a $C_{1-4}$ alkyl group, a $C_{1-4}$ alkoxy group, a benzyloxy group, a phenylsulfonylmethyl group, and a $C_{1-4}$ alkanesulfonyloxy group), a pyridyl-$C_{1-8}$ alkyl group, a $C_{1-8}$ alkoxycarbonyl-$C_{1-8}$ alkyl group, or a carboxy-$C_{1-8}$ alkyl group;

X represents an oxygen atom, an NH group, or an $S(O)_n$ group (wherein n represents an integer of 0, 1, or 2); and m represents an integer from 2 to 8; or a salt thereof.

2. The benzoic acid derivative or the salt thereof according to claim 1, wherein R represents a $C_{1-8}$ alkyl group, a $C_{3-7}$ cycloalkyl-$C_{1-8}$ alkyl group, a $C_{6-10}$ aryl group, a $C_{6-10}$ aryl-$C_{1-8}$ alkyl group (wherein the $C_{6-10}$ aryl moiety may be substituted with one or two groups selected from a halogen atom, a nitro group, and a $C_{1-4}$ alkyl group), or a $C_{6-10}$ aryl-oxy-$C_{1-8}$ alkyl group (wherein the $C_{6-10}$ aryl moiety may be substituted with a halogen atom).

3. The benzoic acid derivative or the salt thereof according to claim 1, which is selected from the group consisting of 3-[3-[N-(Benzoxazol-2-yl)-N-2-(4-chlorophenoxy)ethyl]aminopropoxy]benzoic acid, 2-[5-[N-(Benzoxazol-2-yl)-N-isopropyl]aminopentylthio]benzoic acid, 2-[5-[N-(Benzoxazol-2-yl)-N-n-butyl]aminopentylthio]benzoic acid, and 2-[5-[N-(Benzoxazol-2-yl)-N-n-pentyl]aminopentylthio]benzoic acid, and salts thereof.

4. A pharmaceutical composition comprising a benzoic acid derivative or a salt thereof according to claim 1 and a pharmaceutically acceptable carrier.

5. A therapeutic method for hyperlipidemia comprising administering a benzoic acid derivative or a salt thereof according to claim 1 to a patient in need thereof.

6. A therapeutic method for arteriosclerosis comprising administering a benzoic acid derivative or a salt thereof according to claim 1 to a patient in need thereof.

7. A therapeutic method for diabetes comprising administering a benzoic acid derivative or a salt thereof according to claim 1 to a patient in need thereof.

8. A therapeutic method for diabetic nephropathy comprising administering a benzoic acid derivative or a salt thereof according to claim 1 to a patient in need thereof.

9. A therapeutic method for inflammation comprising administering a benzoic acid derivative or a salt thereof according to claim 1 to a patient in need thereof.

10. A pharmaceutical composition comprising a benzoic acid derivative or a salt thereof according to claim 2 and a pharmaceutically acceptable carrier.

11. A pharmaceutical composition comprising a benzoic acid derivative or a salt thereof according to claim 3 and a pharmaceutically acceptable carrier.

* * * * *